United States Patent
Isaacs et al.

(10) Patent No.: US 10,835,325 B2
(45) Date of Patent: *Nov. 17, 2020

(54) SYSTEM AND METHOD FOR IMAGE LOCALIZATION OF EFFECTERS DURING A MEDICAL PROCEDURE

(71) Applicant: TrackX Technology, LLC, Durham, NC (US)

(72) Inventors: Robert E. Isaacs, Chapel Hill, NC (US); Samuel Morris Johnston, Durham, NC (US); David Alexander Skwerer, Raleigh, NC (US)

(73) Assignee: TrackX Technology, LLC, Durham, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/594,212

(22) Filed: Oct. 7, 2019

(65) Prior Publication Data

US 2020/0030042 A1 Jan. 30, 2020

Related U.S. Application Data

(63) Continuation of application No. 15/596,452, filed on May 16, 2017, now Pat. No. 10,441,367.

(Continued)

(51) Int. Cl.
*A61B 5/05* (2006.01)
*G06K 9/00* (2006.01)
(Continued)

(52) U.S. Cl.
CPC ............... *A61B 34/20* (2016.02); *A61B 6/12* (2013.01); *A61B 6/463* (2013.01); *A61B 6/487* (2013.01);
(Continued)

(58) Field of Classification Search
USPC ........ 382/100, 103, 128–134, 153–155, 168, 382/173, 181, 219, 232, 254, 255, 274,
(Continued)

(56) References Cited

U.S. PATENT DOCUMENTS 7,526,065 B2 * 4/2009 Hardesty ................ G01N 23/04
378/62
7,658,541 B2 * 2/2010 Li ........................ A61B 6/4291
378/204

(Continued)

*Primary Examiner* — Seyed H Azarian
(74) *Attorney, Agent, or Firm* — Maginot, Moore & Beck, LLP

(57) ABSTRACT

A computer-assisted imaging and localization system assists the physician in positioning implants and instruments into a patient's body. The system displays overlapping images—one image of the surgical site with the patient's anatomy and another image showing the implant(s) or instrument(s). The overlapping image of the implant/instrument is moved over the static image of the anatomy as the implant/instrument is moved. These moving image of the implant/instrument can be an unaltered image or an image altered to intensify or mitigate the anatomical or non-anatomical aspects of the moving image. Sliding these images over one another helps the surgeon in positioning devices or instruments with a high degree of accuracy and with a limited number of additional x-rays.

14 Claims, 22 Drawing Sheets

Related U.S. Application Data

(60) Provisional application No. 62/336,999, filed on May 16, 2016, provisional application No. 62/374,187, filed on Aug. 12, 2016.

(51) Int. Cl.
*A61B 34/20* (2016.01)
*A61B 6/12* (2006.01)
*A61B 90/00* (2016.01)
*A61B 6/00* (2006.01)

(52) U.S. Cl.
CPC ............ *A61B 6/5235* (2013.01); *A61B 90/37* (2016.02); *A61B 6/4441* (2013.01); *A61B 6/5205* (2013.01); *A61B 2034/2055* (2016.02); *A61B 2034/2065* (2016.02); *A61B 2034/2072* (2016.02); *A61B 2090/365* (2016.02); *A61B 2090/373* (2016.02); *A61B 2090/376* (2016.02); *A61B 2090/3764* (2016.02); *A61B 2090/3937* (2016.02); *A61B 2090/3966* (2016.02); *A61B 2090/3983* (2016.02)

(58) Field of Classification Search
USPC ................ 382/285, 291, 305, 312; 345/419; 378/145, 4, 21, 204; 600/426, 424
See application file for complete search history.

(56) References Cited

U.S. PATENT DOCUMENTS

| | | | |
|---|---|---|---|
| 7,853,305 B2 * | 12/2010 | Simon | A61B 34/20 600/424 |
| 7,885,441 B2 * | 2/2011 | Node-Langlois | G06T 7/30 382/128 |
| 2008/0269602 A1 * | 10/2008 | Csavoy | A61B 34/20 600/426 |
| 2013/0113791 A1 * | 5/2013 | Isaacs | G06T 3/20 345/419 |

* cited by examiner

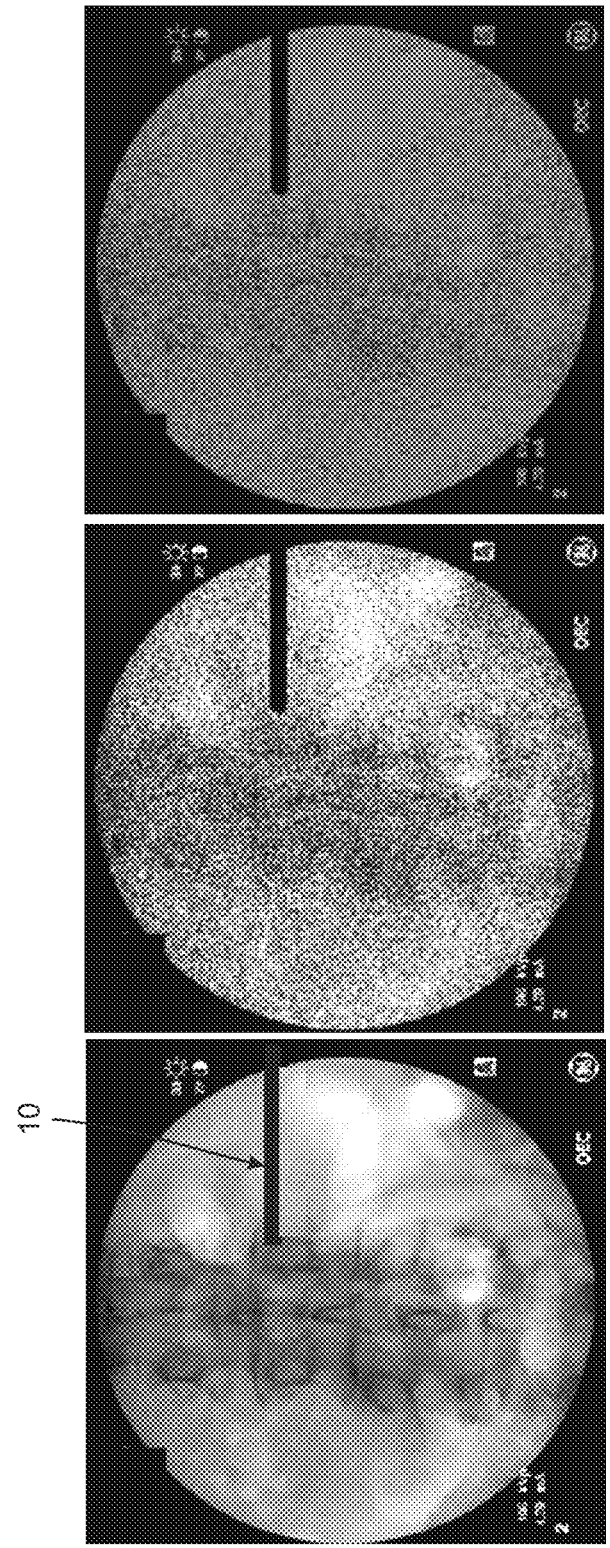

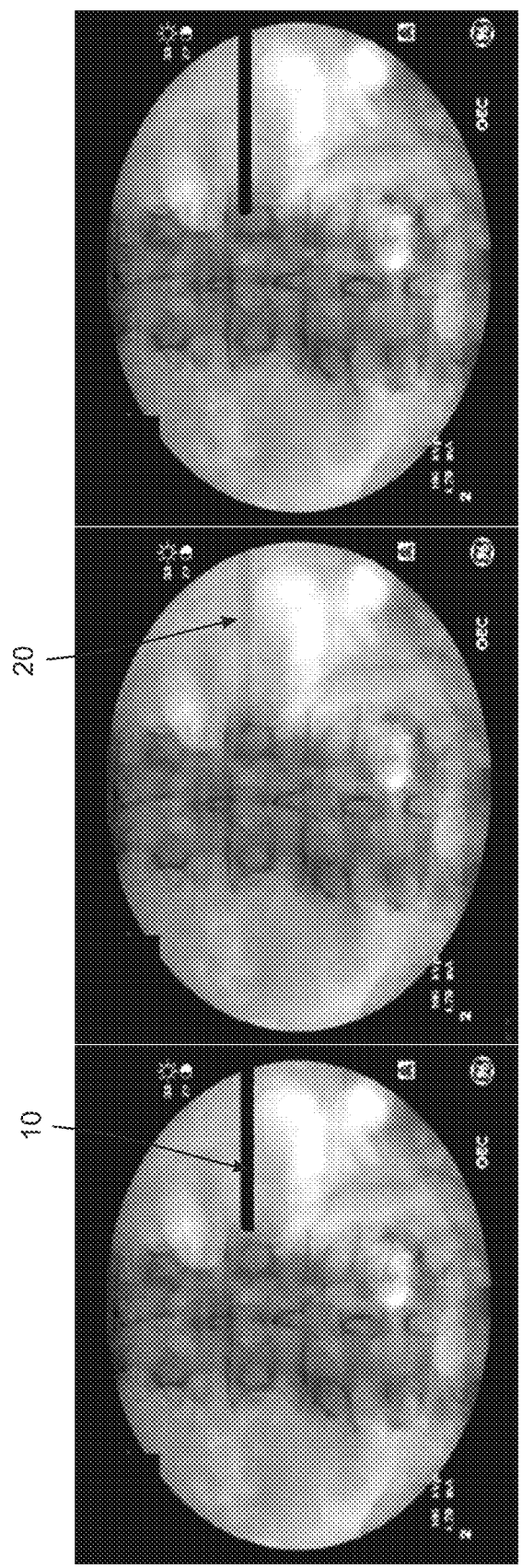

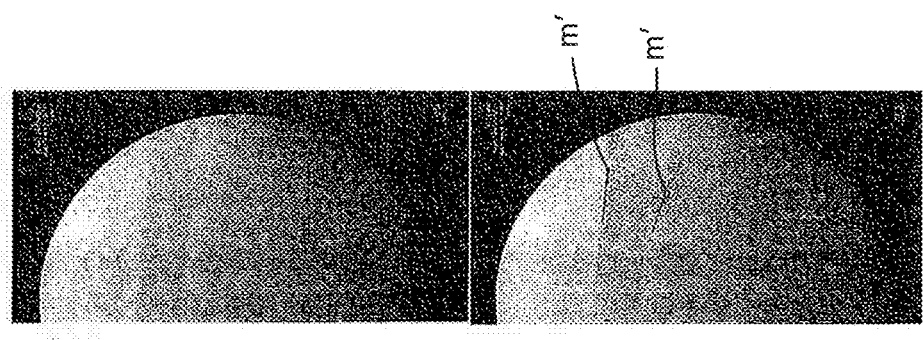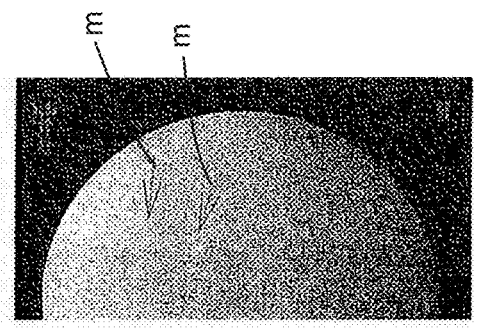

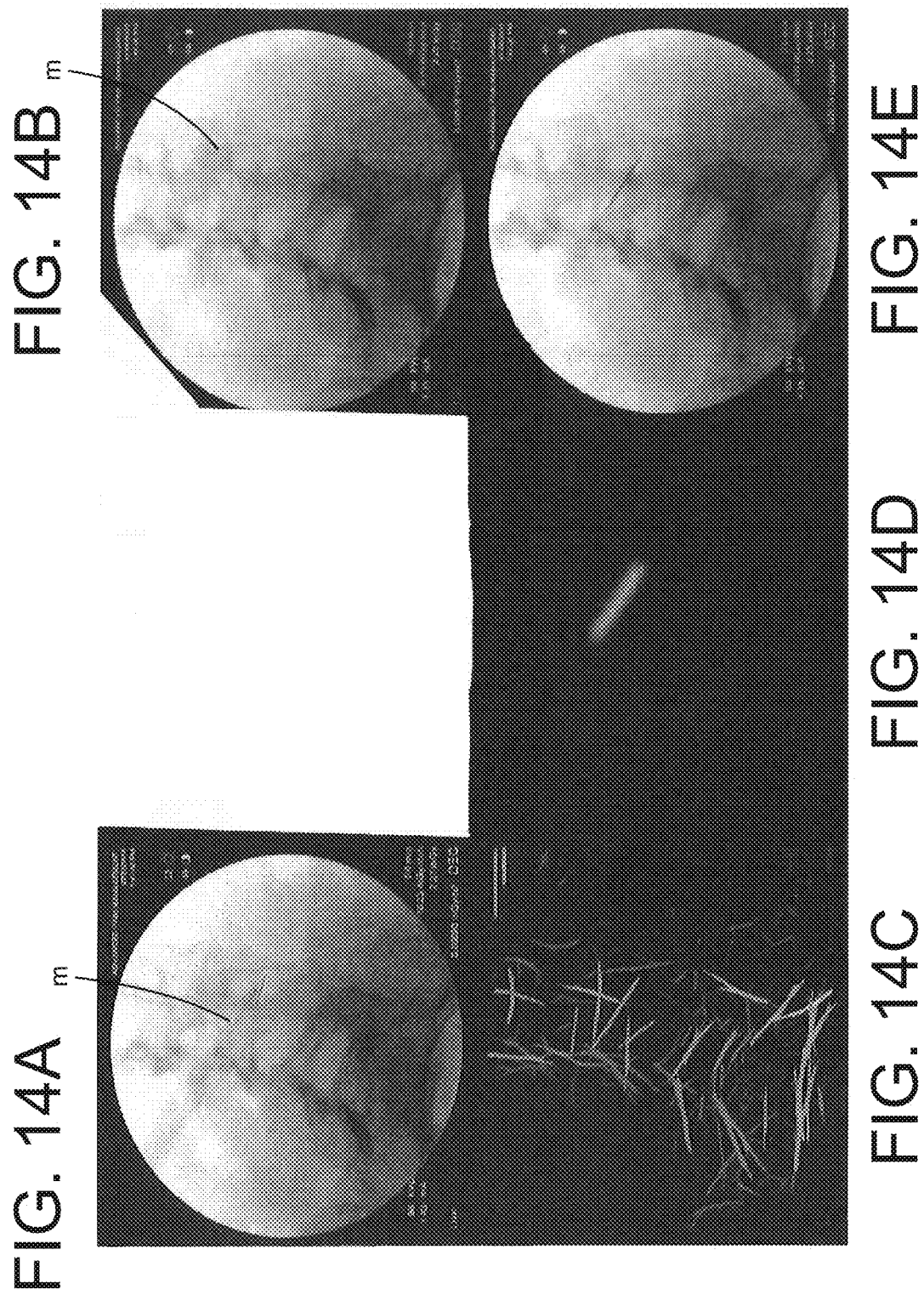

SYSTEM AND METHOD FOR IMAGE LOCALIZATION OF EFFECTERS DURING A MEDICAL PROCEDURE

PRIORITY CLAIM AND REFERENCE TO RELATED APPLICATIONS

This application is a continuation application of and claims priority to co-pending U.S. patent application Ser. No. 15/596,452, entitled "System and Method for Image Localization of Effecters During a Medical Procedure," filed on May 16, 2017, the entire disclosure of which is incorporated herein by reference. The co-pending U.S. patent application Ser. No. 15/596,452 is a utility filing from and claims priority to U.S. Provisional Application No. 62/336,999, entitled "System and Method for Image Localization of Effecters During a Medical Procedure," filed on May 16, 2016, the entire disclosure of which is incorporated herein by reference. The co-pending U.S. patent application Ser. No. 15/596,452 is also a utility filing from and claims priority to U.S. Provisional Application No. 62/374,187, entitled "Detection of Tracked Metal Objects During Imaging," filed on Aug. 12, 2016, the entire disclosure of which is incorporated herein by reference.

BACKGROUND

Many surgical procedures require obtaining an image of the patient's internal body structure, such as organs and bones. In some procedures, the surgery is accomplished with the assistance of periodic images of the surgical site. Surgery can broadly mean any invasive testing or intervention performed by medical personnel, such as surgeons, interventional radiologists, cardiologists, pain management physicians, and the like. In surgeries and interventions that are in effect guided by serial imaging, which we will refer to as image guided, frequent patient images are necessary for the physician's proper placement of surgical instruments, be they catheters, needles, instruments or implants, or performance of certain medical procedures. Fluoroscopy, or fluoro, is one form of intraoperative X-ray and is taken by a fluoro unit, also known as a C-arm. The C-arm sends X-ray beams through a patient and takes a picture of the anatomy in that area, such as skeletal and vascular structure. It is, like any picture, a two-dimensional (2D) image of a three-dimensional (3D) space. However, like any picture taken with a camera, key 3D info may be present in the 2D image based on what is in front of what and how big one thing is relative to another.

A DRR is a digital representation of an X-ray made by taking a CT scan of a patient and simulating taking X-rays from different angles and distances. The result is that any possible X-ray that could be acquired for that patient can be simulated, which is unique and specific to how the patient's anatomical features look relative to one another. Because the "scene" is controlled, namely by controlling the virtual location of a C-Arm to the patient and the angle relative to one another, a picture can be generated that should look like any X-ray taken in the operating room (OR).

Many imaging approaches, such as taking fluoro images, involve exposing the patient to radiation, albeit in small doses. However, in these image guided procedures, the number of small doses adds up so that the total radiation exposure can be problematic not only to the patient but also to the surgeon or radiologist and others participating in the surgical procedure. There are various known ways to decrease the amount of radiation exposure for a patient/surgeon when an image is taken, but these approaches come at the cost of decreasing the resolution of the image being obtained. For example, certain approaches use pulsed imaging as opposed to standard imaging, while other approaches involve manually altering the exposure time or intensity. Narrowing the field of view can potentially also decrease the area of radiation exposure and its quantity (as well as alter the amount of radiation "scatter") but again at the cost of lessening the information available to the surgeon when making a medical decision. Collimators are available that can specially reduce the area of exposure to a selectable region. For instance, a collimator, such as the Model Series CM-1000 of Heustis Medical, is placed in front of an x-ray source, such as the source 104 shown in FIG. 1. The collimator consists of a series of plates that absorb most incident X-rays, such as lead. The only x-rays that reach the patient are those that pass through apertures between the plates. The position of the plates can be controlled manually or automatically, and the plates may be configured to provide differently shaped fields, such a multi-sided field. Since the collimator specifically excludes certain areas of the patient from exposure to x-rays, no image is available in those areas. The medical personnel thus have an incomplete view of the patient, limited to the specifically selected area. Thus, while the use of a collimator reduces the radiation exposure to the patient, it comes at a cost of reducing the amount of information available to the medical personnel.

A typical imaging system 100 is shown in FIG. 1. The imaging system includes a base unit 102 supporting a C-arm imaging device 103. The C-arm includes a radiation source 104 that is positioned beneath the patient P and that directs a radiation beam upward to the receiver 105. It is known that the radiation beam emanated from the source 104 is conical so that the field of exposure may be varied by moving the source closer to or away from the patient. The source 104 may include a collimator that is configured to restrict the field of exposure. The C-arm 103 may be rotated about the patient P in the direction of the arrow 108 for different viewing angles of the surgical site. In some instances, radio-dense effecters, such as metal implants or instruments T, may be situated at the surgical site, necessitating a change in viewing angle for an unobstructed view of the site. Thus, the position of the receiver relative to the patient, and more particularly relative to the surgical site of interest, may change during a procedure as needed by the surgeon or radiologist. Consequently, the receiver 105 may include a tracking target 106 mounted thereto that allows tracking of the position of the C-arm using a tracking device 130. For instance, the tracking target 106 may include several infrared emitters spaced around the target, while the tracking device is configured to triangulate the position of the receiver 105 from the infrared signals emitted by the element. The base unit 102 includes a control panel 110 through which a radiology technician can control the location of the C-arm, as well as the radiation exposure. A typical control panel 110 thus permits the technician to "shoot a picture" of the surgical site at the surgeon's direction, control the radiation dose, and initiate a radiation pulse image.

The receiver 105 of the C-arm 103 transmits image data to an image processing device 122. The image processing device can include a digital memory associated therewith and a processor for executing digital and software instructions. The image processing device may also incorporate a frame grabber that uses frame grabber technology to create a digital image or pixel-based image for projection as displays 123, 124 on a display device 126. The displays are positioned for interactive viewing by the surgeon during the procedure. The two displays may be used to show images from two views, such as lateral and AP, or may show a baseline scan and a current scan of the surgical site. An input device 125, such as a keyboard or a touch screen, can allow the surgeon to select and manipulate the on-screen images. It is understood that the input device may incorporate an array of keys or touch screen icons corresponding to the various tasks and features implemented by the image processing device 122. The image processing device includes a processor that converts the image data obtained from the receiver 105 into a digital format. In some cases the C-arm may be operating in the cinematic exposure mode and generating many images each second. In these cases, multiple images can be averaged together over a short time period into a single image to reduce motion artifacts and noise.

Standard X-ray guided surgery typically involves repeated x-rays of the same or similar anatomy as an effecter (e.g.—screw, cannula, guidewire, instrument, etc.) is advanced into the body. This process of moving the effecter and imaging is repeated until the desired location of the instrument is achieved. This iterative process alone can increase the lifetime risk of cancer to the patient over 1% after a single x-ray intensive intervention.

Classic image guided surgery ("IGS") uses prior imaging as a roadmap and projects a virtual representation of the effecter onto virtual representations of the anatomy. As the instrument is moved through the body, the representation of the effecter is displayed on a computer monitor to aid in this positioning. The goal is to eliminate the need for x-rays. Unfortunately, in practice, the reality of these devices doesn't live up to the desire. They typically take significant time to set-up, which not only limits adoption but only makes them impractical for longer surgeries. They become increasingly inaccurate over time as drift and patient motion cause a disassociation between physical space and virtual space. Typical IGS techniques often alter work flow in a significant manner and do not offer the physician the ability to confirm what is occurring in real-time and to adjust the instrument as needed, which is a primary reason fluoroscopy is used.

What would benefit greatly the medical community is a simple image localizer system that helps to position instruments without altering workflow. It would be substantially beneficial if the system can quickly be set-up and run, making it practical for all types of medical interventions both quick and protracted. The desirable system would significantly limit the number of x-rays taken, but does not require eliminating them. Therefore, by both encouraging reimaging and using this as a means to recalibrate, the system would ensure that the procedure progresses as planned and desired. Using the actual x-ray representation of the effecter rather than a virtual representation of it would further increase accuracy and minimize the need for human interaction with the computer. If the system mimics live fluoroscopy between images, it would help to position instruments and provide the accuracy of live imaging without the substantial radiation imparted by it.

SUMMARY OF THE DISCLOSURE

A computer-assisted imaging localization system is provided that assists the physician in positioning implants and instruments into a patient's body. The system has the desired effect of displaying the actual instrument or implant and using this displayed to guide surgery without the need to directly interact with the computer. The system does so by displaying and moving overlapping images on a computer screen, allowing one image to be seen through the other. These image "masks" can be the unaltered image or doctored images to intensify or mitigate the anatomical or non-anatomical aspects of the image. Sliding these images over one another can help to position medical devices with a high degree of accuracy with a limited number of additional x-rays.

In another feature, a tracking element is provided that is mountable on the shaft of an effecter. The tracking element includes marker bands that substantially encircle the effecter shaft that are configured for sensing by an optical tracking device. In one aspect, the configuration of one or more marker bands on the tracking element can provide indicia of the nature of the effecter. This indicia can be used by the image processing software to determine the nature of the displays and data manipulation provided by the software.

BRIEF DESCRIPTION OF THE DRAWINGS

FIGS. 4A-C are screen shots of x-ray images of a surgical site and radio-dense effecter, including a low dose x-ray image and an image in which the display of the radio-dense effecter is enhanced relative to the image of the anatomy.

FIGS. 5A-C are screen shots of x-ray images in which the radio-dense effecter is represented by a metal mask in an image that moves relative to the fixed image of the surgical site as the effecter moves.

FIGS. 12A-C are screen shots of low dose x-ray images showing images of radio-dense effecters.

FIGS. 14A-E are a series of screen shots of an x-ray image in which the radio-dense effecters are automatically detected by the image processing device of the present disclosure.

DETAILED DESCRIPTION

Figure 1:
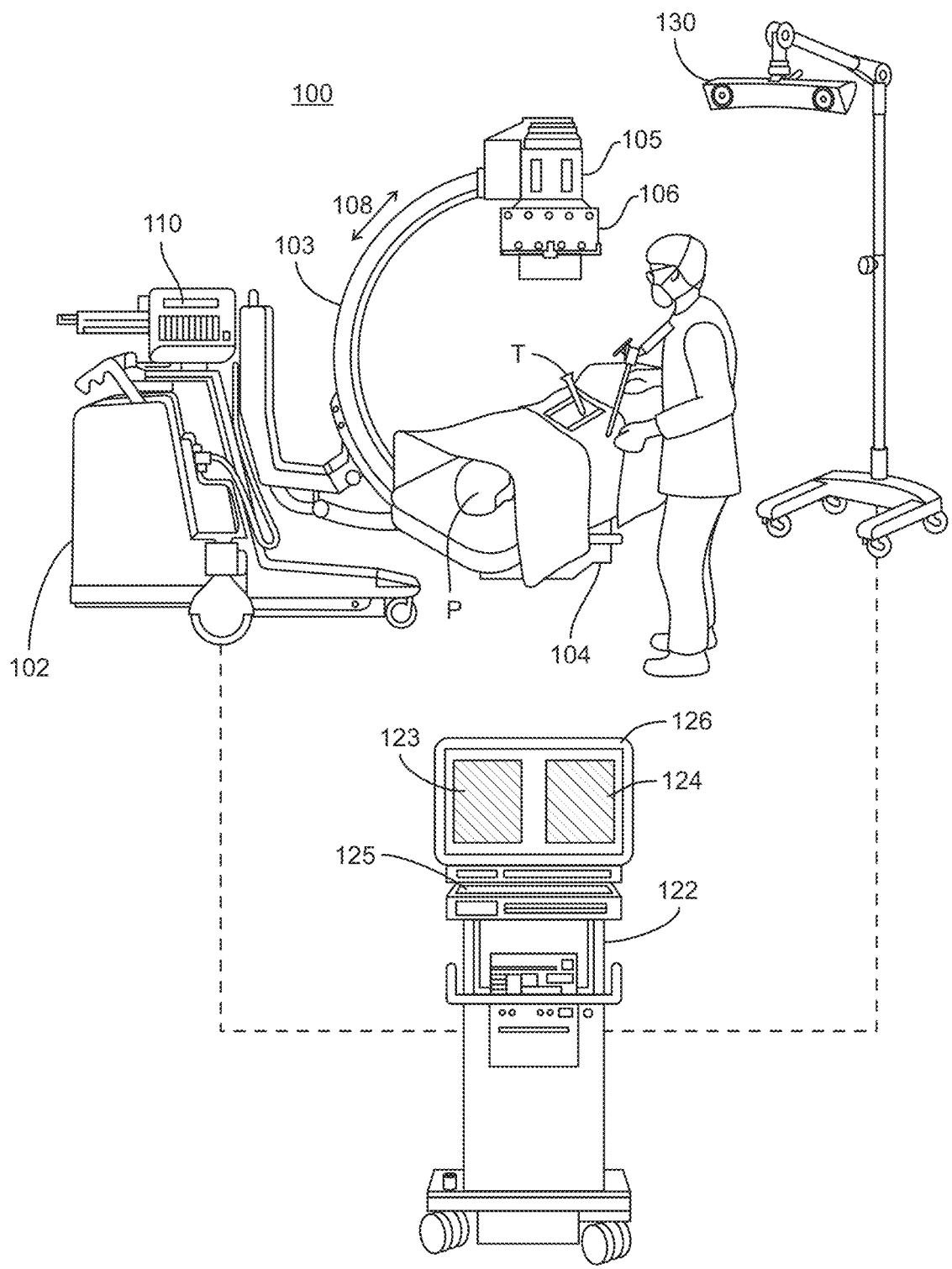
FIG. 1 is a pictorial view of an image guided surgical setting including an imaging system, an image processing device and a localizer or tracking device for surgical instruments and devices.

For the purposes of promoting an understanding of the principles of the disclosure, reference will now be made to the embodiments illustrated in the drawings and described in the following written specification. It is understood that no limitation to the scope of the disclosure is thereby intended. It is further understood that the present disclosure includes any alterations and modifications to the illustrated embodiments and includes further applications of the principles disclosed herein as would normally occur to one skilled in the art to which this disclosure pertains.

Figure 3A:
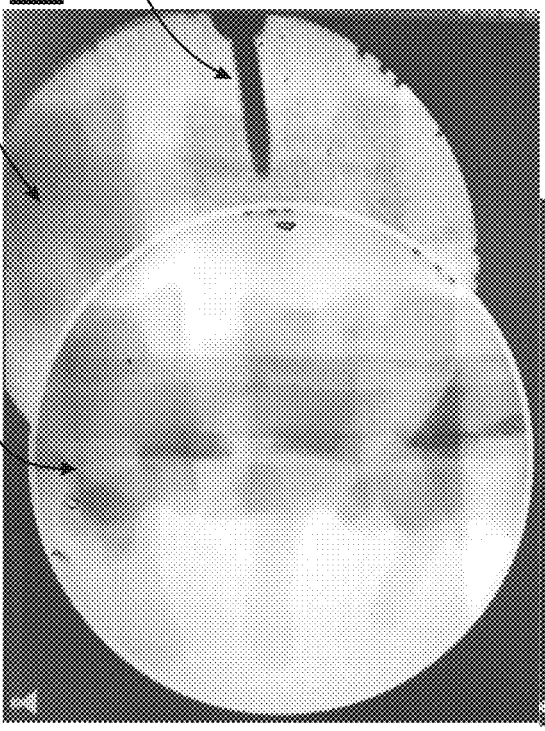
FIGS. 3A-D are screen shots of image displays of a surgical site showing the patient's anatomy and a movable image of a radio-dense effecter in relation to a fixed image of the surgical site.

According to one aspect of the invention, the process begins with taking an image of the anatomy to be addressed surgically. Typically this "localizing shot" or "baseline image" does not contain the radio-dense effecter (e.g.— screw, cannula, guidewire, instrument, etc.) that is to be moved/adjusted, although in one embodiment a single image containing the effecter can be used. The image processing device 122 (FIG. 1) generates a digital image that can be displayed and manipulated digitally. With the anatomy identified and displayed on a computer screen, a "new" image with the effecter or instrument is taken, with this image also converted to a digital image by the image processing device 122. This new image is displayed on top of the original localizing shot so that the resulting image looks like the conventional image on a fluoroscope screen, such as shown in FIG. 3A. In one aspect of the present disclosure, the effecter, such as effecter T in FIG. 1, incorporates a localizer system (e.g.—EM, Optical IGS, etc) capable of tracking movement of the effecter. The 3D movement of the effecter measured by the localizer system can be applied to the digital representation of the "new" image relative to move the "new" image relative to the "localizing shot" image. Thus, as the tip of the effecter is tracked, the movement of the "new" image shows the change in position of the tip of the instrument being tracked relative to the stationary anatomy depicted in the "localizing shot". On the computer screen, it thus appears as if live fluoroscopy is being taken as the effecter is being moved and as if the actual tool or implant is being moved and adjusted relative to the patient's anatomy. When the next image is taken, the tip of the effecter is at the location that the physician desires. It can be appreciated that unlike the typical IGS system in which a digital model of the effecter is manipulated, the system and method of the present disclosure relies on manipulating an actual image of the effecter in the surgical field.

Figure 2:
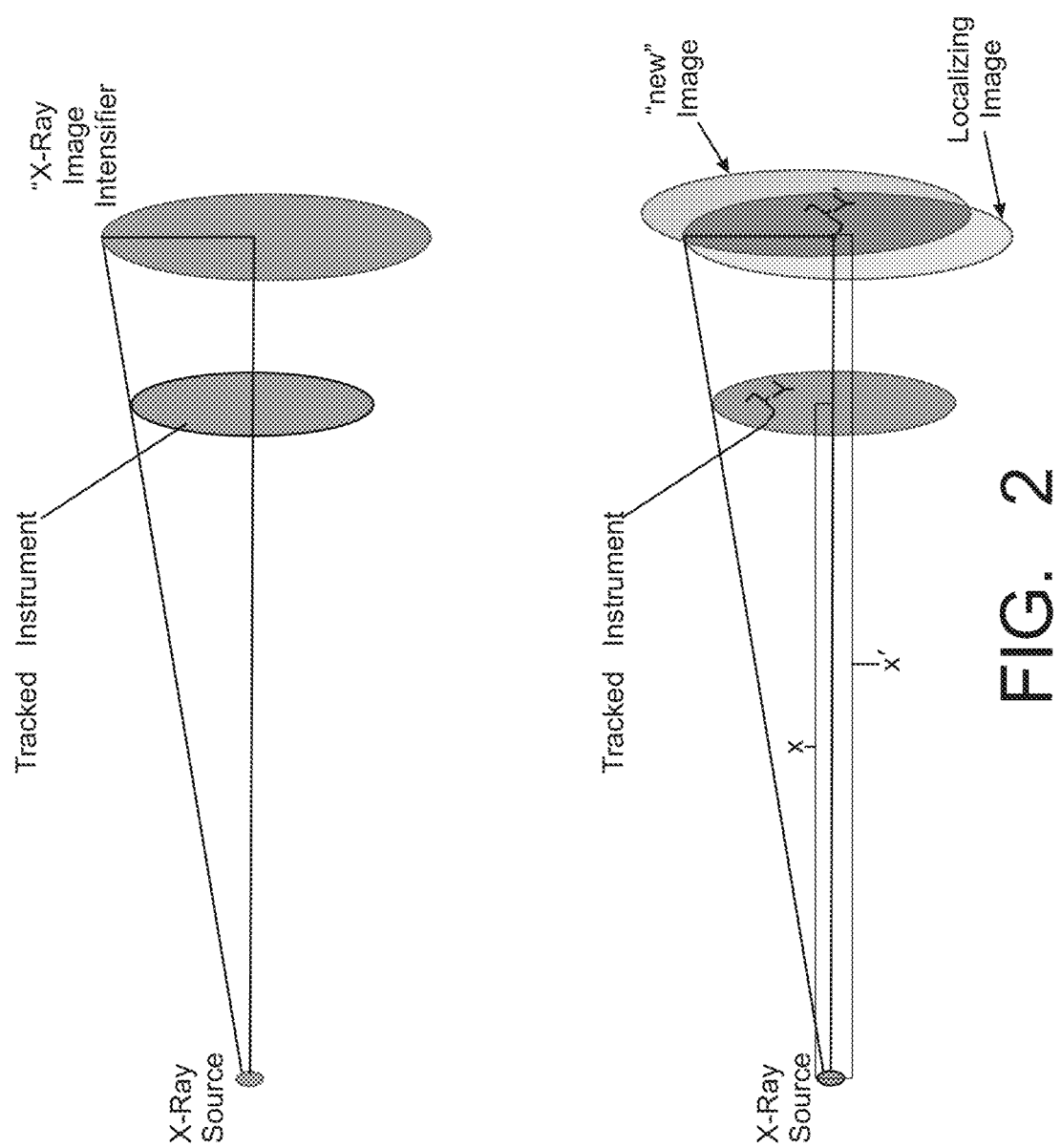
FIG. 2 is a diagram of steps in displaying movement of a tracked effecter on an x-ray image of a surgical site.

The movement of the "new" image on the display is based on the geometry of the tip of the effecter relative to the location within the cone beam of the fluoroscope, as depicted in FIG. 2. The nearer the tip of the tracked effecter is to the x-ray source, for the same relative movement, the greater the movement of the "new" image and therefore the effecter's projection (in pixels) relative to the size of the "localizing shot". Assuming a standard size image, such as a 9 in. image intensifier, and assuming a typical 1000 mm separation of the x-ray source from the intensifier, there is an approximate 2.24 pixel per mm movement of the tracked effecter projected on the image intensifier. Away from the image intensifier and closer to the source, this pixel-per-mm movement ratio is magnified in a consistent manner as shown in FIG. 2. In particular, the movement distance of the projection of the tracked effecter on the image intensifier is given by $Y'=X'*Y/X$, where Y is the actual movement distance of the effecter, X is the distance from the source to the tracked effecter/instrument, X' is the distance from the source to the localizing image at the image intensifier and Y' is the projected movement distance. It can be appreciated that the distance X' is typically fixed throughout the procedure for a conventional C-arm X-ray source. The distance X and the movement distance Y can be determined by the image processing device 122 (FIG. 1) based on data received from the localizer system used to track the movement of the effecter. The image processing device uses the projected movement distance Y' to move the "new" image accordingly on the display.

The "new" image, shown in the lower representation in FIG. 2, can be taken using standard x-ray settings, or may be taken using less than full dose radiation or low dose settings which has the benefit of blurring out the anatomy while having relatively little impact on the image of an effecter in the image. (It is understood that a "radio-dense" material generally does not allow the imaging rays or x-rays to pass through so that the radio-dense effecter blocks the underlying anatomy). When the "new" image is a low dose image, the "new" image can be combined with or overlaid on the image from the localizing shot allowing the user to see the resulting combined image with the appearance of the anatomy appearing as a live fluoroscopic image. The result is an image as seen in FIG. 3A that can help guide an effecter to the correct location desired by the physician.

In the example shown in FIGS. 3A-D, a bone screw 10 to be tracked is introduced into a patient after an initial "localizing shot" and projected on the display 122/123 (FIG. 1) as the screen shot of FIG. 3A. As the tracked instrument 10 is moved out of the field of the localizing shot or baseline image 12, as depicted in the screen shot of FIG. 3B, the two overlapping images can be appreciated, with the localizing shot 12 seen to the left and the new low radiation image 14 to the right. It can be noted that the metal screw in the low radiation image is very prominent while the representation of the anatomy is obscure. When the tracked screw is moved into an ideal location based on the desire of the physician, such as shown in the screen shot of FIG. 3C, the image on the screen can constantly project a combined image (overlaying the full dose localizing shot with the low dose image) that replicates what a new fluoroscopic image would look like at any point, mimicking live fluoroscopy without obtaining a new live image. It can be appreciated that the localizing or baseline image 12 does not change as the effecter 10 is moved, at least so long as the C-arm or X-ray source is not moved. Thus, the digital data for the localizing image 12 is not manipulated by the image processing device during movement of the effecter. On the other hand, the image processing device does manipulate the digital data of the "new" image based on the projected movement of the tracked effecter so that the "new" image moves across the display as the effecter is moved.

Figure 3B:
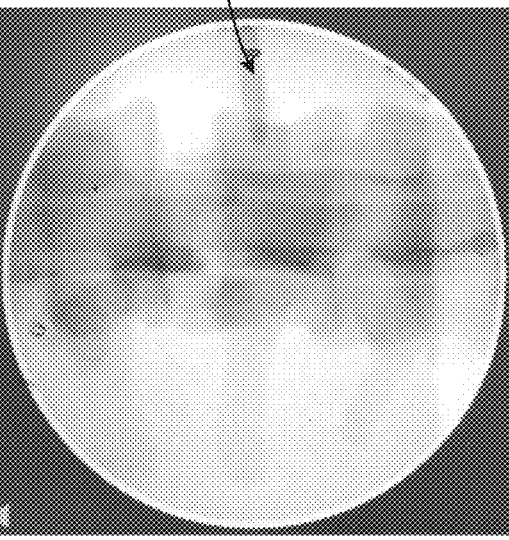
Figure 3C:
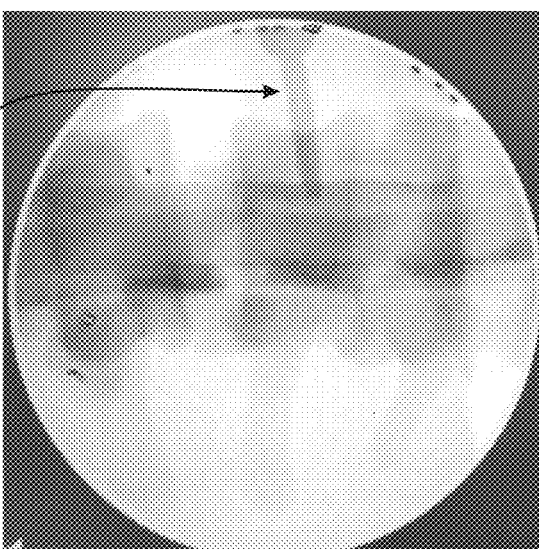
Figure 3D:
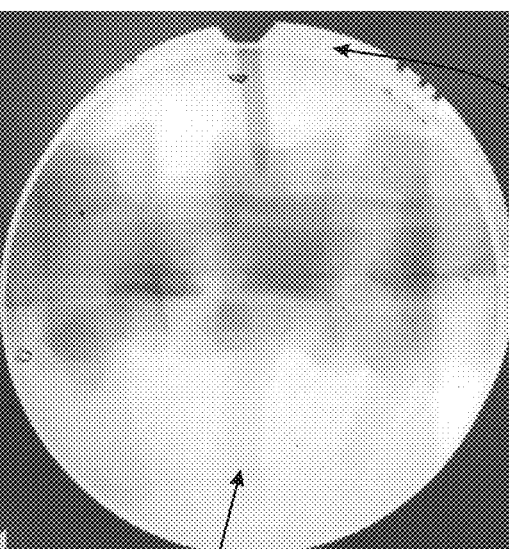

A stationary full dose new image can be taken, such as the display in the screen shot of FIG. 3D, to confirm that the effecter 10 is in the location desired by the physician. If for some reason the image alignment is off or further fine tuning is required, this newly acquired image can replace the prior localizing shot image as the baseline image, and the process is repeated. The system thus resets or recalibrates when the full dose new image is taken, so that subsequent images are always more accurately displayed than previous ones.

It can be appreciated that as the physician moves the effecter 10 the low dose image moves with the effecter. When the effecter is within the field of the baseline or localizing shot image, as in FIG. 3C, the image of the effecter from the low dose image is combined with the stationary localizing image so that the physician can clearly see the patient's anatomy and the effecter's position relative to that anatomy. As the effecter is moved within the field of the baseline image, the image of the effecter (and the "new" image) moves accordingly so that the physician can guide the tip of the effecter to the desired position in the anatomy. It is contemplated that the overlaid images can be in two displays with two views of the surgical site, such as an AP view and a lateral view, for instance. The baseline and subsequent new images can be acquired as both AP and lateral views. As the effecter is moved, its associated image is moved in both displayed views so that the surgeon can observe the 3D movement of the effecter.

In recognition that a new image is not actually being acquired during each step of movement of the effecter, the physician can acquire new low dose images at various stages of movement of the effecter to verify the actual location of the effecter. Thus, any error in the actual vs. displayed position of the effecter relative to the anatomy is eliminated with each new low dose image taken. In other words, with each low dose image, the system recalibrates the actual position of the effecter relative to the anatomy based on the digital data acquired from the low dose image. The new data identifying the new position of the effecter is then the starting point for movement of the new image as the effecter is moved by the surgeon. It is contemplated that the physician may require multiple low dose images as the effecter is moved into its final position, with each low dose image recalibrating the actual position of the effecter, potentially culminating in a full dose image to verify the final position.

Although a low radiation image is shown in FIGS. 3A-D, a conventional or full dose "new" image can be taken and displayed with similar results, as shown in the screen shot of FIG. 4A. A low radiation image can be used, as see in the screen shot of FIG. 4B, or a metal intensification of the "new" image can be performed as shown in the screen shot of FIG. 4C. The image of FIG. 4B is obtained under low radiation so that the anatomic features are effectively washed out. While the image of the effecter 10 is also washed out due to the low dosage, the metal or other radio-dense material is sufficiently radiopaque so that the resulting image of the effecter in FIG. 3B is still outstanding enough to be easily seen.

The image of FIG. 4C is generated by intensifying the pixels associated with the image of the effecter 10, so that when the full image is displayed the image of the effecter essentially washes out the image of the underlying anatomy. In either case, what is projected has the ability to "fool the eye" to make it appear to the surgeon as if the instrument is moving under live fluoroscopy.

The metal intensification image of FIG. 4C can constitute a metal mask applied to the images, such as the image in the screen shot of FIG. 5A. As shown in FIG. 5B, the image of the effecter 10 is represented by a green mask 20 overlaying the actual image. The movement of the mask is correlated to the actual movement of the effecter as determined by the localizer. When the green layer of the mask 20 is moved to a more ideal location, a confirmatory x-ray can be taken as in the screen shot of FIG. 5C. The green or metal mask 20 can be generated by the image processing device 122 (FIG. 1) using software that examines the pixels of the image to determine which pixels are associated with anatomic features and non anatomic features based primarily on the intensity value of each pixel. Various filters can be applied each pixel of the digitized X-ray image to enhance the edges between pixels representing anatomic and non-anatomic features. Once the pixels associated with the non-anatomic features are acquired and the edges enhanced, the pixels outside the selected non-anatomic pixels can be washed out, leaving only the pixels for the non-anatomic feature corresponding to the effecter.

Figure 6A:
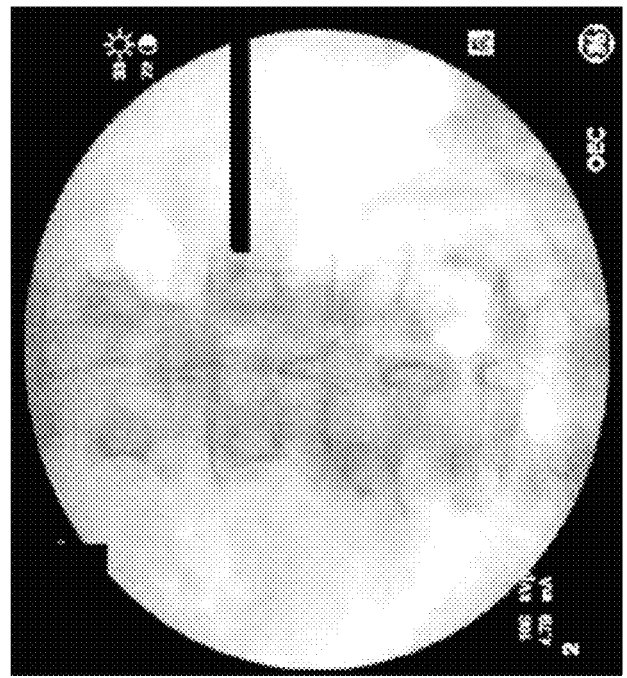
FIGS. 6A-B are screen shots of x-ray images of the surgical site with an overlaying metal mask image of the effecter.

Similar to the images of FIGS. 5A-C, image tracking can be applied in FIGS. 6A_B to a Jamshedi needle 10' that is repositioned to a desired position in the patient's body. However, in FIG. 6A there is no initial "localizing shot". The "new" image serves as both the stationary and the moved image. The image of the effecter is replaced by a green layer mask, such as the mask 20 of FIG. 5C, and just the green layer of the image is moved on the background of the "new" image. The image guidance system of the effecter can determine the relative location of the instrument in the image, so that rather than moving the entire image as in the prior examples, only a narrow area around the region of the effecter 10' is moved.

Figure 6B:
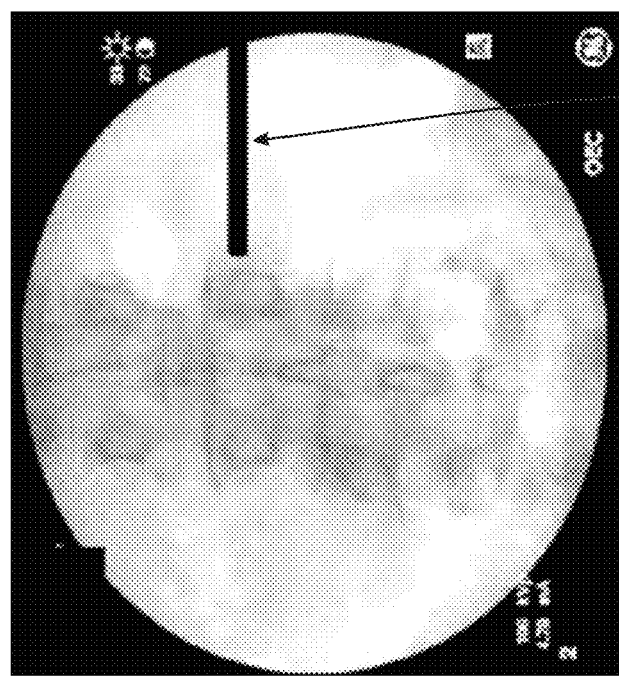

The present invention contemplates a system and method for moving image masks or overlapping image sets based on the movement of a tracked object, which provides the physician or surgeon with the ability to place a surgical effecter at the correct location inside a patient with a minimal number of X-ray images. Movement projection is not based on the absolute motion of the effecter but rather on the relative motion of the tracked effecter within the imaging space. Although knowledge of the absolute location of the tip of the effecter is needed for certain image movements, such as shown in FIG. 6B, such knowledge is not necessary. It is only necessary to know the relative motion between the original position and the new position of the effecter, and the distance from the tip of the effecter/instrument to the X-ray source.

The position of the effecter/instrument can be recalibrated on each new X-ray shot. On the instrument side this means that each x-ray resets the relative position or the initial starting point of the "new" image to the current location of the tracked effecter to which is linked a "new" image with that effecter in it. This feature makes the system mostly focused on relative movement so that the potential time horizon for drift to set in is minimized.

The system and method disclosed herein creates "pseudo-live fluoroscopy", meaning that the physician/surgeon can see the movement of the effecter/instrument in real-time without constant imaging of the patient. The present disclosure further contemplates automating taking images to create constantly re-updated spot images with "pseudo-live fluoroscopy" in between to create a continuous high accuracy instrument tracking device with a live fluoroscopy appearance with dramatically fewer images and resulting radiation. The methods of the present disclosure only require knowledge of relative movement (meaning the delta between the last position of the instrument to the current) and only require displaying the 2D motion of the effecter/ "new" image to make this functional. The present disclosure provides a more comprehensive imaging system compared to typical IGS where it is necessary to know the absolute movement and the actual knowledge of what is being moved (in order to project a correct virtual representation of it).

The system and method of the present invention works with a metal mask or an actual image, and can work with low dose images or full dose images. With this system, the entire image can be moved or adjusted, as shown in FIGS. 3, 4, or only a region of interest is moved or adjusted, as shown in FIG. 6B.

The system and method disclosed herein uses the actual effecter (or more specifically an active x-ray picture of the effecter), not a virtual representation of it as in a typical IGS. This approach makes it possible to emphasize or deemphasize different features (e.g.—anatomy, metal, etc) of the two images to aid in visualization. The methods disclosed herein do not require distortion correction or dewarping, or a calibration phantom, as is often required in typical IGS. Thus, the present system does not require a grid on the c-arm to correct for the various types of distortion (i.e.—pin cushion, etc.). When an IGS system is being used, the present system permits the IGS tracker to be either placed at the tip of the effecter (in the case of an EM microsensor or the like) or projected to the tip by a known offset that is more typical of an optical system. The present system does not require any patient reference, such as a "beacon" that is standard on nearly all IGS systems. In particular, it is not necessary to know the location of the object's tip relative to the c-arm (the distance of the tip between the image intensifier and the x-ray source) and the in plane movement (distance and trajectory) of the effecter The present system and method can operate with a single image, separating metal or other radio-dense material from anatomy and leaving the anatomy without the metal or other radio-dense material as a layer, or the metal or other radio-dense material can be moved without anatomy as a layer, as depicted in FIGS. 5, 6, or the layers can be moved in any combination.

The present method and system even works with distorted IGS data (like is classically a problem with EM), as the movement won't be perfect but will asymptotically get closer to the correct position. For instance, if the IGS data is inaccurate by 20%, then after the first movement, a "new" x-ray will confirm that it is 20% off. However, the system is then recalibrated so that now moving the new "new" image is not only more accurate, but the distance needed to move is only $\frac{1}{5}^{th}$ the prior distance. Thus, even if the system still has a 20% error, the next movement to close the gap of this 20% will be only 4% off (i.e., 20% of 20%). The use of relative motion and this perpetually smaller distance moved between each x-ray allows the present system to use noisy warped EM data for application in the OR.

Figure 7:
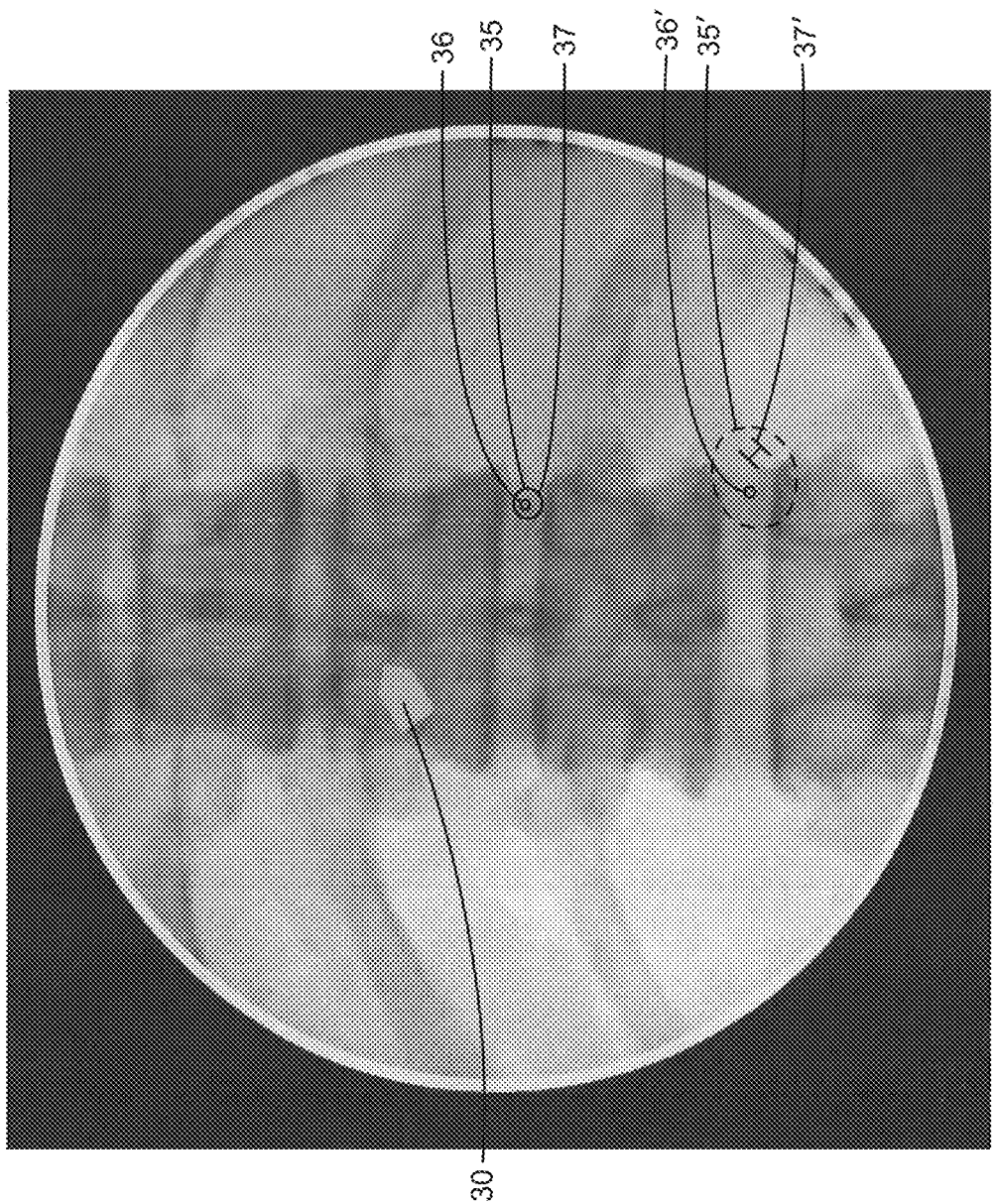
FIG. 7 is a screen shot of an x-ray image with slugs indicating the position of the tip of radio-dense effecters relative to the anatomy shown in the image.

In another feature, the tip of the effecter, such as effecter 10, can be represented on the displayed x-ray image as a slug 30 shown in the screen shot of FIG. 7. The position of the slug can correspond to the position of the tip of the effecter relative to the anatomy and can take various forms, including a circle or bulls-eye and an arrow, as depicted in FIG. 7. The appearance of the slug 30 can be varied to signify different conditions in the process of navigating the effecter to the desired anatomical position. For instance, the size or configuration of the slug can be indicative of the degree of accuracy associated with the particular movement. For example, the slug can be depicted as a circle when the accuracy is lower and an arrow when the accuracy is greater. The size of the circle can be related to the degree of accuracy for the location of the tip of the effecter.

The color of the slug can be also varied to indicate certain conditions, namely conditions of the C-arm or x-ray device. For example, the slug can be green if the current position of the C-arm is within a narrow range of its position, 2 mm for instance, when the localizing image was acquired, and red if the current position is outside that range. When the slug changes from green to red the physician can obtain a new x-ray image to establish a new baseline and verify the actual current position of the effecter. As long as the color of the effecter remains green the physician can have confidence that the actual location of the effecter tip corresponds to the displayed location. As an alternative to changing color, the slug 30 can flash if the position of the C-arm has changed.

In the case where multiple effecters are present in a surgical site, the color of the slug 30 can be indicative of the particular effecter associated therewith. It should be appreciated that all of the steps discussed above can be implemented for multiple effecters for accurate navigation of the effecters to a desired position. It can be expected that the multiple effecters may require positioning and re-positioning during a procedure, so methods of the present disclosure can be modified accordingly to account for multiple effecters and multiple slugs.

In another embodiment, a slug 35, shown in FIG. 7, marking the location of the tip of the effecter can include a central element 36, in the form of a dot or small circle, corresponding to the position of the tip, and a second element 37, in the form of a circle that is at least initially concentrically disposed around the central element 36. The second element in the form of a circle can correspond to a point on the effecter offset along the longitudinal axis of the effecter from the tip. The location of the second element or circle 37 relative to the central element or dot 36 provides the physician with an indication of the attitude of the effecter. In the depiction of FIG. 7, the offset of the circle 37 relative to the dot 36 indicates that the shaft of the associated effecter extends to the left and downward in the surgical field.

In an alternative embodiment, a slug 35' can include the same first element in the form of a dot or small circle 36' depicting the position of the effecter tip, as shown in FIG. 7. However, rather than include a circle for the second element, the second element of the slug 35' is an "I" that not only indicates the orientation of the effecter relative to its tip, but also indicates the rotation about the axis of the effecter. The angular offset of the "I" from a vertical orientation provides the surgeon with a visual indication of the rotational orientation of the implant, tool or instrument.

Figure 8:
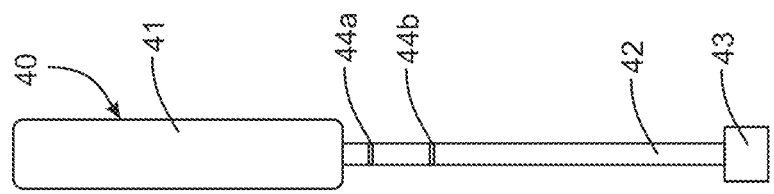
FIG. 8 is a side view of a generic effecter having marker bands used for tracking the position of the effecter.

As discussed above, the present systems and methods utilize tracking information from a localizer system that acquires the position of the effecter. Typical localizer systems utilize an array of optical sensors to track an optical tracking component mounted to the end of the effecter. This arrangement is cumbersome and often interferes with the surgeon's field of view of the surgical site. In one aspect of the present disclosure, an effecter 40 includes a handle 41 with an elongated shaft 42 terminating in a working tip 43, as depicted in FIG. 8. The shaft 42 is provided with optically trackable markers 44a, 44b in the form of optical bands that at least partially encircle the shaft. It is contemplated that the bands encircle at least 300° around the shaft so that the markers are visible at all rotational angles of the effecter. The bands may be formed by optical tape applied to the effecter or may be applied directly to the material of the effecter, such as by etching. The two markers 44a, 44b permit tracking the movement of the effecter in five degrees of freedom—X, Y, Z, pitch (X rotation) and yaw (Y rotation). The markers 44a, 44b are provided at a predetermined distance from the working tip 43 so that the localizer software can use the detected location of the two markers to extrapolate the 5 DOF position of the working tip.

In one aspect of this feature of the invention, the markers 44a, 44b are separated by a predetermined spacing in which the spacing is indicative of the type of effecter. For instance, one spacing of the markers may denote a cage inserter while another different spacing of the markers may denote a distracter. The localizer system can be configured to discern the spacing of the markers 44a, 44b and then refer to a stored data base to determine the nature of the effecter being detected. The data base includes information locating the working tip in relation to the markers so that the position of the working tip can be accurately determined by sensing the location of the markers. The data base may also include a model of the instrument that can be used to generate the metal mask 20 described above. Once the particular effecter is identified, the localizer system will always know where the working tip is located even when one of the two markers is obscured. Alternatively, the width of one or more of the bands may be indicative of the nature of the effecter being detected.

Figure 9:
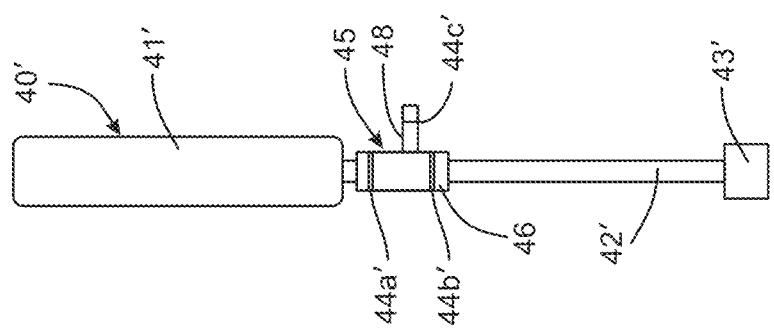
FIG. 9 is a side view of a generic effecter having a tracking element mounted on the effecter and providing marker bands for tracking the position of the effecter.

In another aspect, the markers are incorporated into a tracking element 45 that can be mounted to the shaft 42' of a tool 40' that is otherwise similar to the tool 40, as shown in FIG. 9. The tacking element includes a cylindrical or partially cylindrical body 46 that can be clipped onto the shaft 42' and held in position with a friction grip. The cylindrical body 46 includes the two markers 44a', 44b' in the form of bands that encircle the body. A third marker 44c' can be provided on an arm 48 that projects from the cylindrical body, with the third marker constituting an optically detectable band. The addition of the third marker 44c' adds a sixth degree of freedom to the position data detected by the localizer device, namely roll or rotation about the Z-axis or longitudinal axis of the shaft 42'. The bands 44a', 44b' can be spaced apart in the manner described above to denote a particular effecter.

Figure 10:
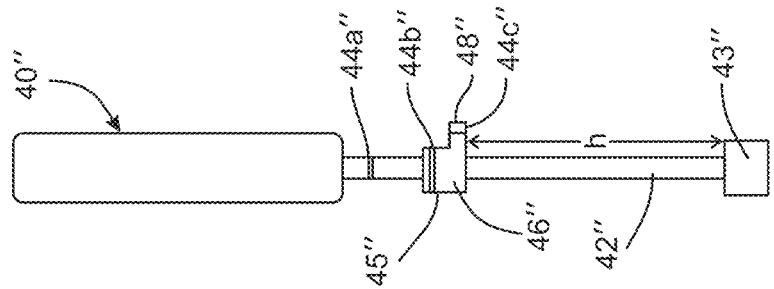
FIG. 10 is a side view of a generic effecter having another tracking element mounted on the effecter and providing marker bands for tracking the position of the effecter.

In an alternative embodiment, an effecter 40" shown in FIG. 10 includes an existing conventional fiducial marker 44a" on the shaft 42" of the effecter. A tracking element 45" includes a cylindrical or partially cylindrical body 46" configured to be clamped onto the shaft 42" of the effecter. The body 46" includes a second marker 44b" in the form of a band that encircles the cylindrical body, and may include a third marker 44c" on a perpendicular extension 48". The two markers 44b", 44c" on the tracking element 45" cooperate with the existing fiducial 44a" on the effecter to permit detecting the position of the effecter, and therefore the working tip 43", in six degrees of freedom. In this embodiment, the tracking element 45" is clamped to the shaft 42" at a particular height h relative to the working tip 43". The height h produces a predetermined spacing relative existing fiducial 44a", which spacing can be used to identify the nature of the particular effecter. A calibration tool may be used to position the tracking element 45" at the proper height for a particular effecter.

As mentioned, the location of the markers on the effecter can be used to identify the nature of the effecter—i.e., as a tool, instrument, implant etc. The imaging software remembers what effecters are in the surgical field as well as the positions as they are moved within that field. Even if one of more of the markers are temporarily blocked from view of the localizer or tracking device, the imaging software can extrapolate the position of the effecter based on the position of the available markers.

In a further aspect of the invention, the image processing software can be configured to automate certain features of the system based on the type of effecter detected and the nature of the procedure. The software can permit the surgeon to identify the nature of the surgical procedure, and then this information together with the information regarding the effecter or effecters in use can be used to toggle certain display features. The toggled features can include metal enhancement (as discussed herein), the nature of the slugs displayed on the x-ray image, or the use of one or two adjacent views (such as AP and lateral at the same time).

Figure 11:
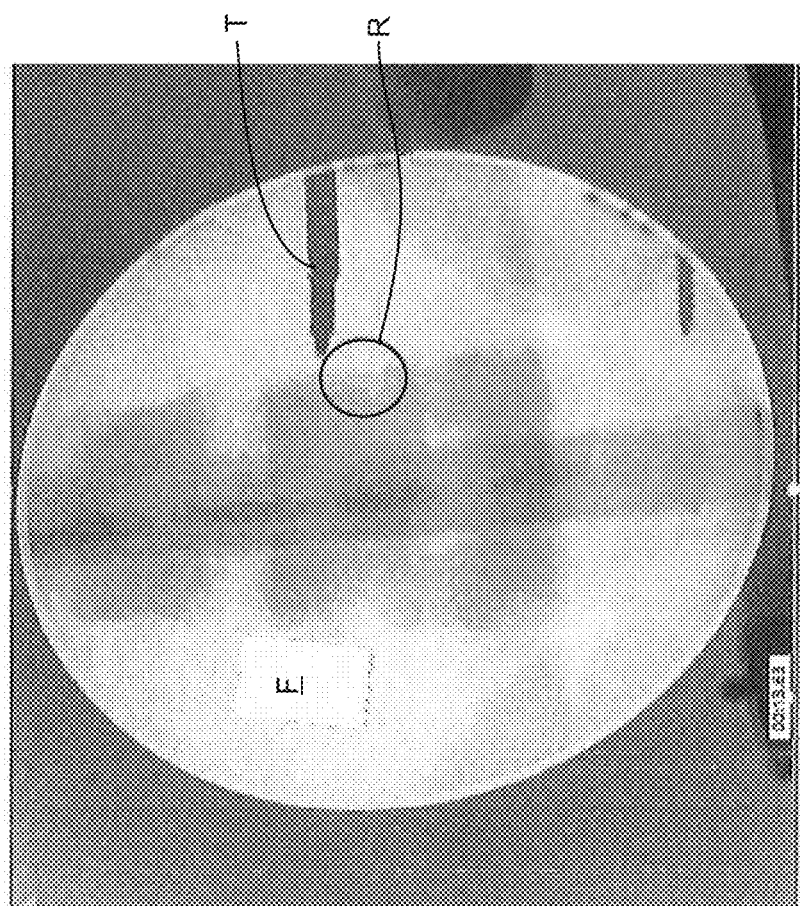
FIG. 11 is screen shot of an x-ray image of a surgical field with an effecter and a region of interest within the viewing field.

The system described above provides a method for tracking an effecter, such as a tool T within a displayed field F, as illustrated in FIG. 11. The present disclosure further contemplates imaging software implemented by the image processing device 22 (FIG. 1) that is activated only when the tracked radio-dense object, such as tool T, enters the surgical field F and a new image has been taken by the radiologist or surgeon. When these two conditions occur, an object mask for the tool, such as the green mask 20, is displayed and the image may be manipulated by the surgeon based on manipulations of the effecter or other radio-dense object. The software remains activated until a new image is taken that does not include the tracked instrument. If the radio-dense object reappears in the field F, the software remembers the original location of the field and the tool and allows manipulation by the radiologist or surgeon.

The software of the present disclosure thus provides a metal identification feature that is always running in the background of the imaging software execution. The software automatically identifies the presence of a radio-dense object in the surgical field without any operator intervention, and displays an image of the radio-dense object without operator intervention. The present disclosure thus contemplates a system for identifying a radio-dense object in an image field and enhancing the display of that object for the benefit of the surgeon attempting to navigate the object within the surgical field. The software disclosed herein thus identifies the nature and parameters of the radio-dense object without any input or intervention from the radiologist or surgeon. The software analyzes the x-ray image to locate the radio-dense object or objects and then create a mask corresponding to the configuration of the object. When the object is moved, the software can move only the object mask without modifying the underlying image of the surgical field. In one approach, the software utilizes existing tracking data for the guided surgical tool to identify the region of the image field in which the tip of the instrument or tool can be found, and/or a general angle of projection of the tool on the x-ray obtained from the existing tracking data. The present disclosure thus provides a system that can locate a tool T even where the tracking data only identifies a region R within the viewing field F (FIG. 11).

Once the radio-dense object is located, the software and system of the present disclosure enhances or intensifies the image of the radio-dense object. As shown in FIG. 12A, some radio-dense objects M are difficult to see in a low dose image. As shown FIG. 12C, the problem is exacerbated when the low dose image is merged with a prior standard dose image (FIG. 12B), such as according to the techniques described U.S. Pat. No. 8,526,700, which issued on Sep. 3, 2013, the entire disclosure of which is incorporated herein by reference. The present disclosure contemplates software executed by the image processing device 122 (FIG. 1) that identifies the location of the radio-dense object(s) M, even in an image field as shown in FIG. 12A, and then intensifies the radio-dense objects M' in a composite image shown in FIG. 12C so that the radio-dense objects are sufficiently visible to the surgeon. The software can locate the radio-dense object directly from the image FIG. 12A, or can use angle of projection and/or location data provided by an image guidance component, to speed up the process of identifying the location of the radio-dense object(s) M. The system and software disclosed herein thus provides means for locating and enhancing incredibly faint objects within the viewing field, even when the image is a low dose image. Once the radio-dense object(s) M' are located and enhanced, only the enhanced radio-dense object is moved while the underlying baseline or composite x-ray image can remain stationary since only the object is being tracked. It is further contemplated that the tracked objects can be limited to only select ones of the radio-dense objects that may appear in a particular field of view. The non-tracked radio-dense objects can remain un-enhanced and left stationary even as the image moves with the tracked radio-dense objects M'. Moreover, any one or multiples of radio-dense objects in an image can be identified, enhanced and moved independently as independent masks overlying a baseline or composite x-ray image. With this feature, multiple physicians can work simultaneously and together to position radio-dense objects necessary for the surgical procedure, all working from the same underlying stationary baseline or composite x-ray image.

Figure 13A:
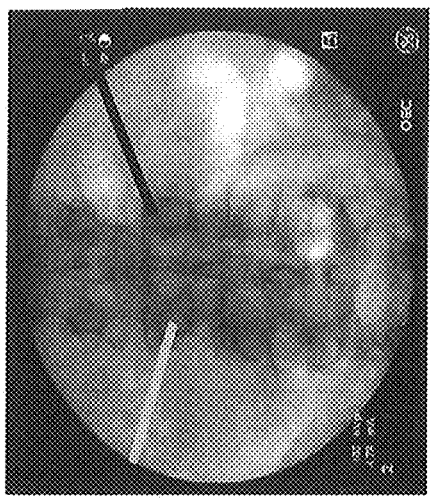
FIGS. 13A-F are screen shots of x-ray images of multiple radio-dense effecters in a surgical field with images of the effecters isolated and represented by metal masks overlaid onto the image of the anatomy.
Figure 13D:
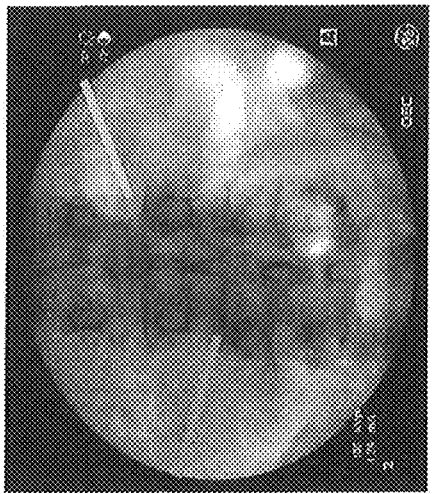
Figure 13B:
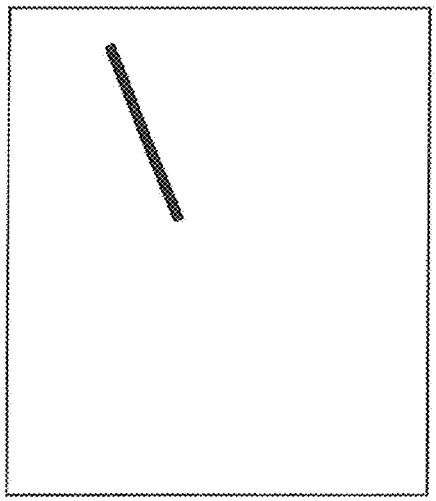
Figure 13E:
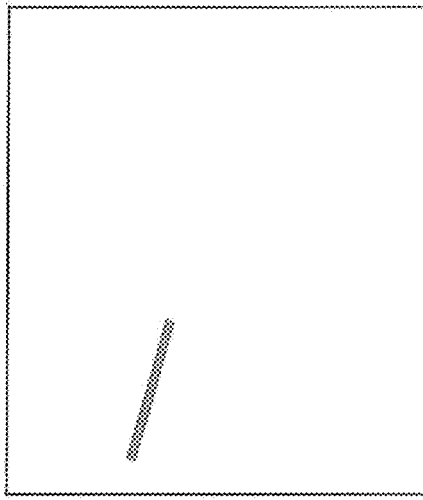
Figure 13C:
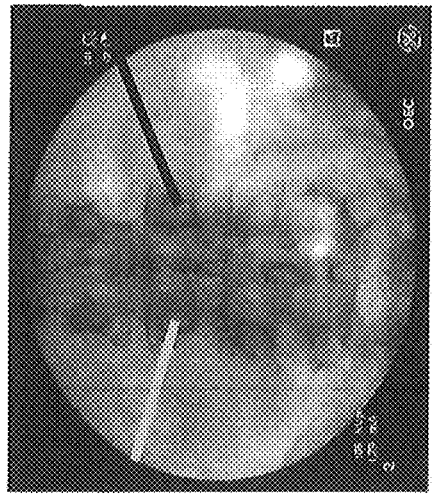
Figure 13F:
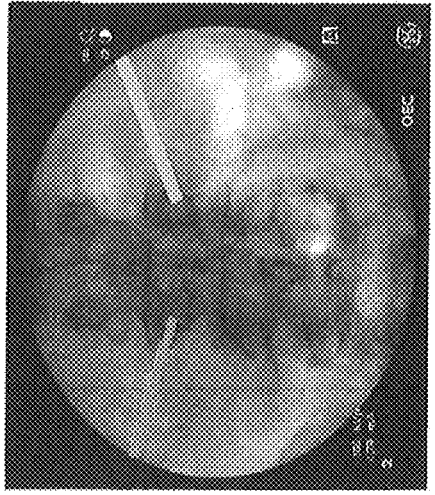

The system and software of the present disclosure allows isolation of a radio-dense object within an image, such as the image FIG. 13A and the isolated image in FIG. 13B. The isolated image can be used to guide movement of the radio-dense object which can then be reintegrated with the x-ray image at a new location as shown in FIG. 13C. This process can be performed with any radio-dense object, once it has been identified, as illustrated in FIGS. 13D-F. The radio-dense objects can be represented by a mask, with the masks for multiple objects being color-coded, as shown in FIG. 13F.

FIGS. 14A-F shows a series of screen shots of displays generated by the present system and software. The first image in FIG. 14A, shows a faint object M in a low radiation image. It is apparent from this image that the radio-dense object M is too faint for a surgeon to reliably manipulate the instrument or tool. In the composite image of FIG. 14B the radio-dense object is even fainter. FIG. 14C shows an image of one step in the metal identification algorithm implemented by the software of the present disclosure which relies on identifying linear edges that are indicative of a non-anatomic feature. When tracking information for the particular effecter or object is added, as shown in FIG. 14D, the correct linear edge is identified as the radio-dense object, which is then enhanced and displayed in the image of FIG. 14E.

Figure 15D:
FIGS. 15B-D are screen shots of an x-ray image showing the movement of the image corresponding to the movement of the c-arm in FIG. 15A.
Figure 15C:
Figure 15B:
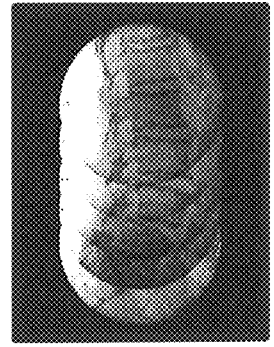
Figure 15A:
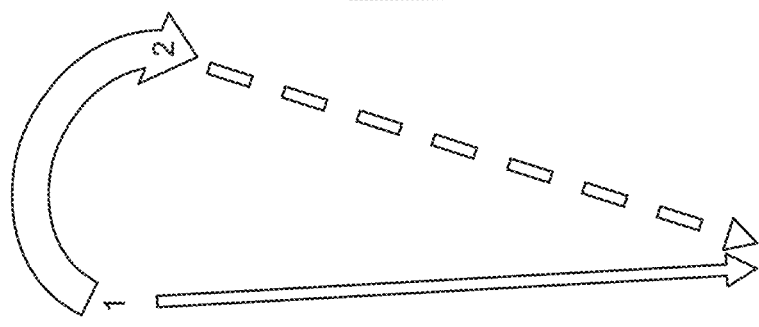
FIG. 15A is a representation of a movement of the x-ray device or c-arm during a surgical procedure.

The system and software further provides two ways to view movement of a tracked radio-dense object within a surgical field. The system described in U.S. Pat. No. 8,526,700, incorporated by reference above, provides a system for orienting a view as the x-ray device or C-arm is angled, as depicted in FIG. 15A. In this system, when the C-arm is moved from position 1 to position 2, the displayed images move from the position in FIG. 15B to the position shown in FIG. 15C. In FIG. 15D, grid lines are added that can ultimately be used to orient the C-arm to a perfect alignment for a Ferguson (flat endplate) view of a spinal field from the orthogonal x-ray image. The grid lines are parallel to the orientation of the effecter or radio-dense object.

Figure 16C:
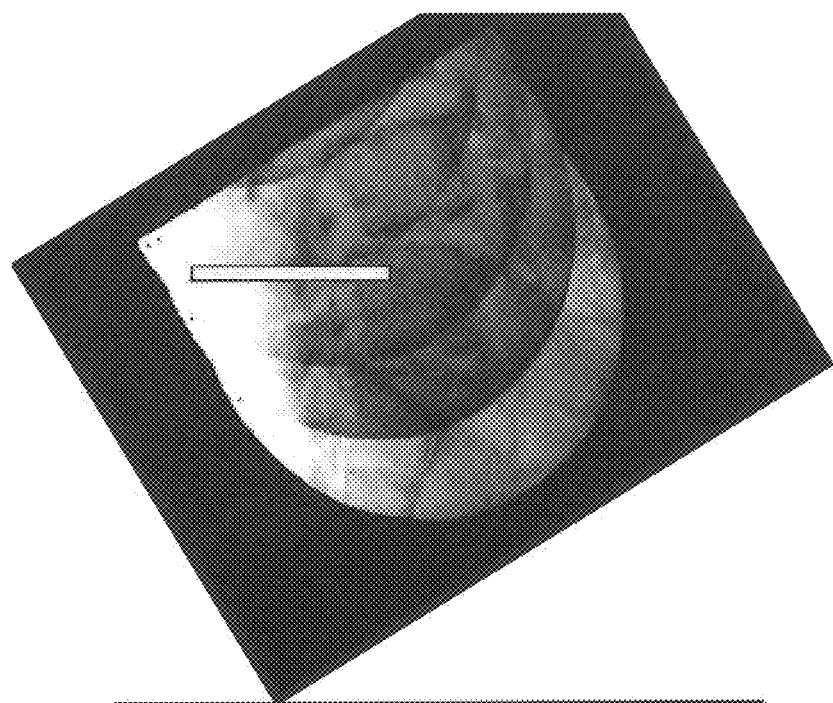
FIGS. 16B-C are screen shots of an x-ray image showing the movement of the image corresponding to the movement of the radio-dense effecter in FIG. 16A with the position of effecter remaining stationary.
Figure 16B:
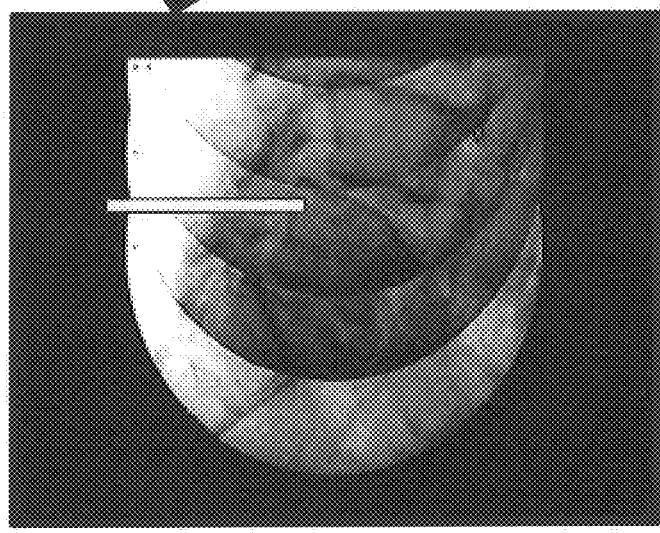
Figure 16A:
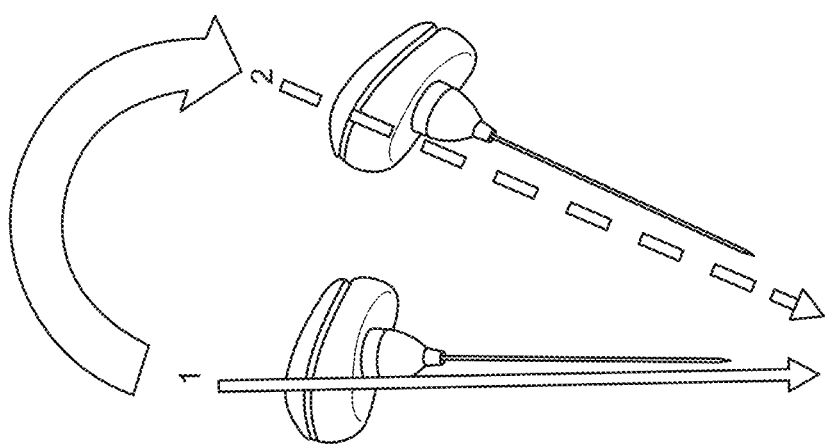
FIG. 16A is a representation of a movement of a radio-dense effecter during a surgical procedure.

In accordance with the present disclosure, when the radio-dense effecter or tool is moved, as shown in FIGS. 16-17, the tracked object controls the angle of the displayed image. The tracked object shown in FIG. 16A is maintained in a constant orientation (such as vertical in FIG. 16B) and the x-ray image itself is rotated commensurate with the movement of the tracked object, as shown in FIG. 16C. It can be appreciated that the change in angular orientation of the image between FIG. 16b and FIG. 16C is the same as the change in angular orientation of the effecter from position 1 to position 2 in FIG. 16A.

As an adjunct to this feature, the image data for the rotated image of FIG. 16C can be used to identify a movement for the c-arm to produce a desired shot of the effecter and the surgical site. For instance, the image data can be used to identify a movement angle for the c-arm to generate an en face view down the shaft of the effecter. Similarly, the image data can be used to center the c-arm over the shaft of the effecter or angle the c-arm to shoot perpendicular to the effecter shaft and centered over the tip of the instrument.

Figure 17C:
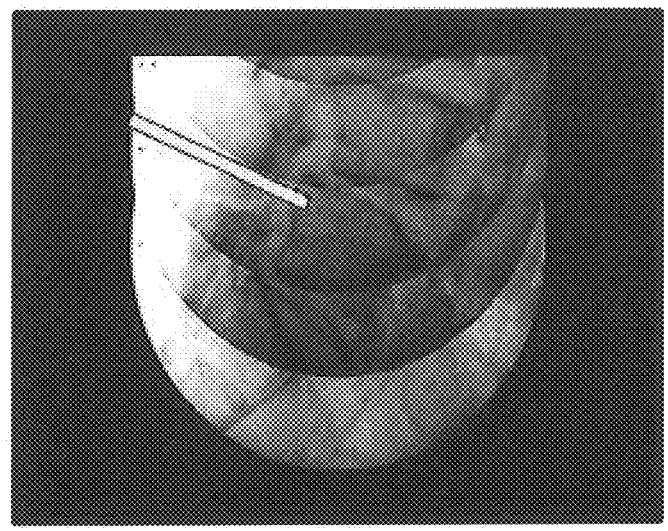
FIGS. 17B-C are screen shots of an x-ray image showing the movement of the image corresponding to the movement of the radio-dense effecter in FIG. 16A with the position of the image of the anatomy remaining stationary.
Figure 17B:
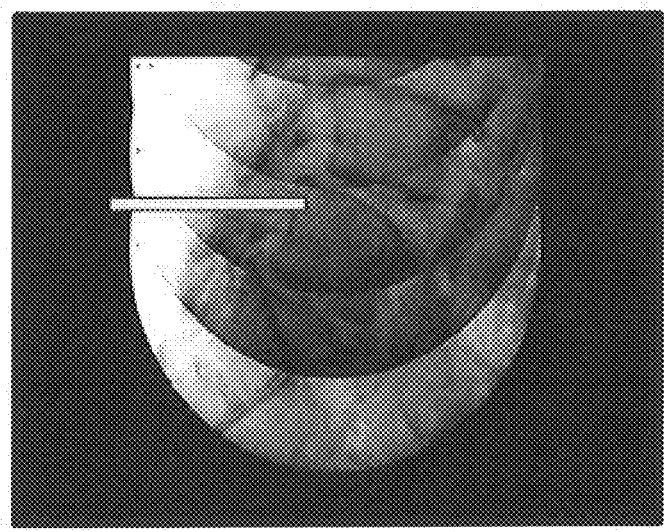
Figure 17A:
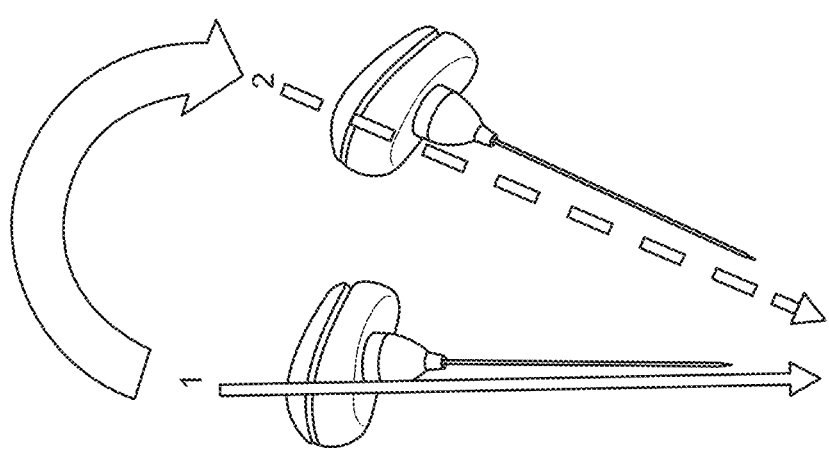
FIG. 17A is a representation of a movement of a radio-dense effecter during a surgical procedure.
Figure 18C:
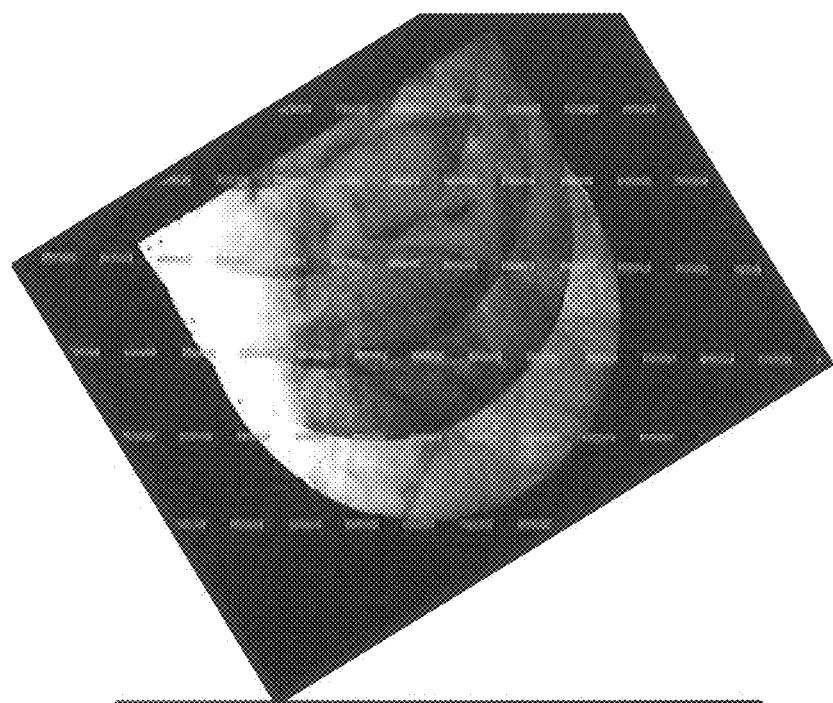
FIGS. 18B-C are screen shots of an x-ray image showing the movement of the image corresponding to the movement of the radio-dense effecter in FIG. 18A with the position of effecter remaining stationary and with grid lines superimposed on the image corresponding to the stationary orientation of the effecter.
Figure 18B:
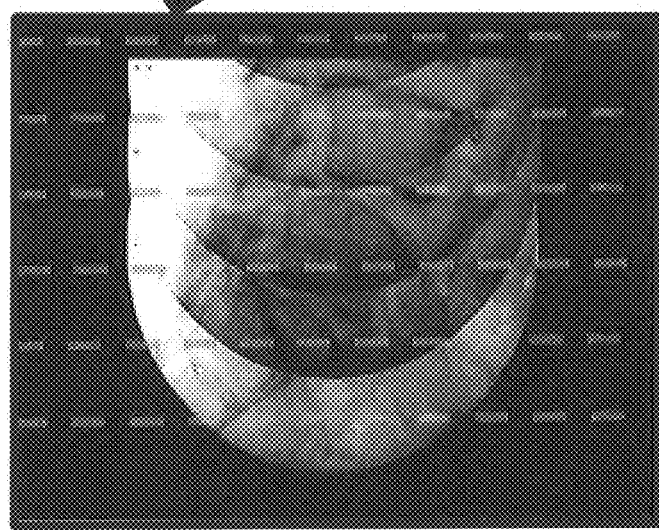
Figure 18A:
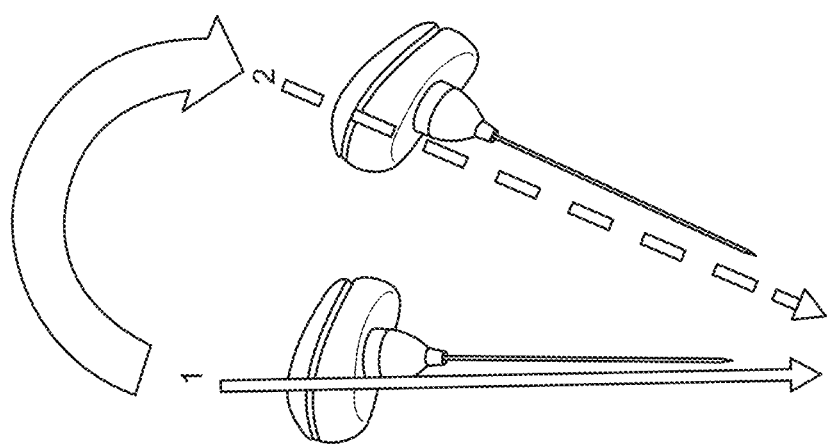
FIG. 18A is a representation of a movement of a radio-dense effecter during a surgical procedure.
Figure 19C:
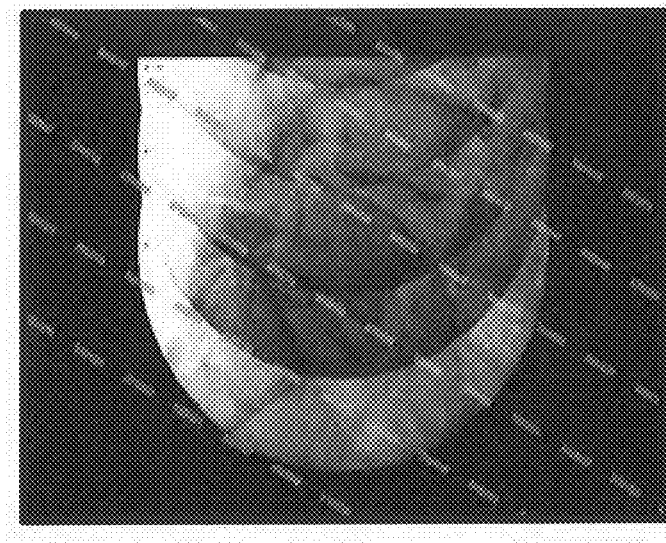
FIGS. 19B-C are screen shots of an x-ray image showing the movement of the image corresponding to the movement of the radio-dense effecter in FIG. 19A with the position of the image of the anatomy remaining stationary and with grid lines superimposed on the image corresponding to the different positions of the radio-dense effecter.
Figure 19B:
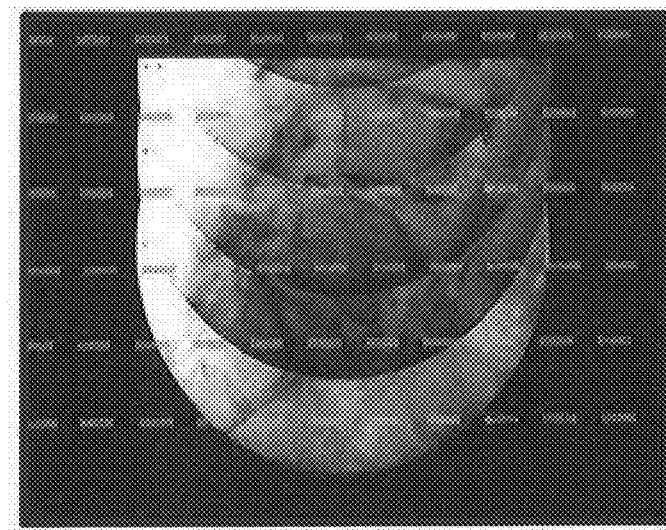
Figure 19A:
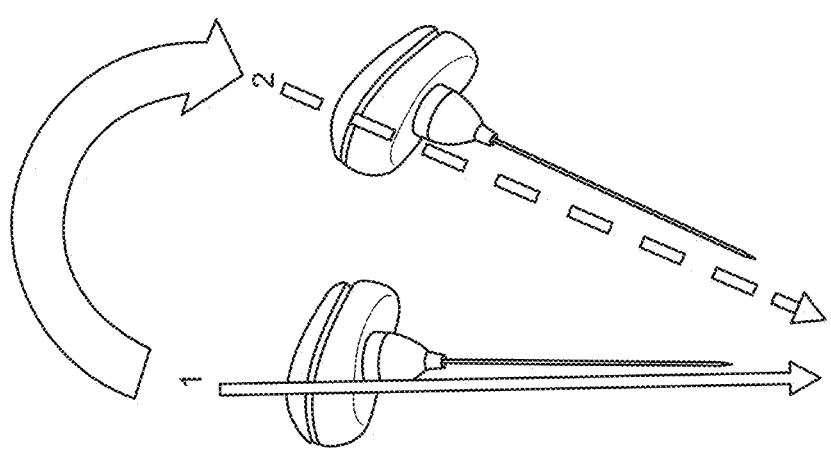
FIG. 19A is a representation of a movement of a radio-dense effecter during a surgical procedure.

Alternatively, as shown in FIGS. 17A-C, the x-ray image can remain stationary while the image or mask of the tracked radio-dense object is moved commensurate with the actual movement of the tracked radio-dense object. The depth of the radio-dense object can be further adjusted by moving the metal mask or image axially along its length. The grid lines can be added to the displays, whether the tracked object remains stationary in the field of view, as in FIGS. 18A-C, or the x-ray view remains stationary and the image or mask of the effecter is moved, as in FIGS. 19A-C.

The grid lines can help illustrate angular movements of the effecter projected into the particular imaging plane (e.g., AP or lateral). As an alternative or adjunct, the display of the image of the moving effecter can be manipulated according to the nature of the movement. When the effecter, or more specifically the tip of the effecter, is moved in an orthogonal direction (x, y, z) the image of the effecter moves linearly. When the effecter is rotated or pivoted relative to the anatomy, the image of the effecter can be skewed in relation to the angle of pivot. Thus, as the effecter pivots in one plane, an image of the effecter in a perpendicular plane skews as the effecter pivots, and more particularly the diameter in the direction of pivoting can shrink and expand as the effecter pivots.

As described above, the imaging software of the present system implements a method to detect the presence and location of tracked radio-dense objects and enhances the objects. The position and orientation of the radio-dense effecter, such as a tool or instrument, in space with respect to an X-ray device are measured by a tracker or localizer system associated with the effecter. This tracking information is used to translate an X-ray image of the effecter on the viewing screen that predicts where the effecter would appear if another X-ray image were acquired. The image of the tool can be merged with a previously acquired image of the patient's anatomy, with the previously acquired image remaining static. The resulting merged image informs the physician about the placement of the effecter relative to the anatomy.

Figure 20:
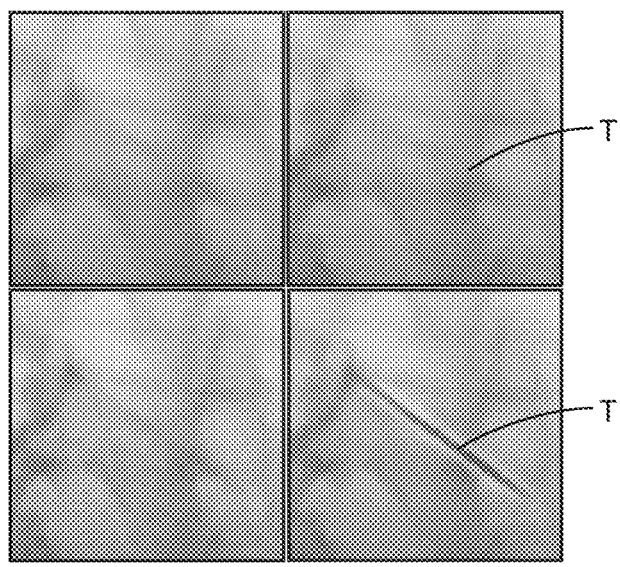
FIG. 20 are screen shots of x-ray images illustrating the low visibility of certain radio-dense effecters in a surgical site.

One problem with this approach is that certain commonly used surgical tools T can be difficult to see in an X-ray image, especially if this image was acquired at a low X-ray dosage, as depicted in the screen shot images of FIG. 20. The visibility of the surgical tool is further diminished by the merging of a baseline image with a subsequent low dose image. Consequently, the present disclosure contemplates a method for enhancing the visibility of a tracked surgical tool in a merged X-ray image.

Figure 21:
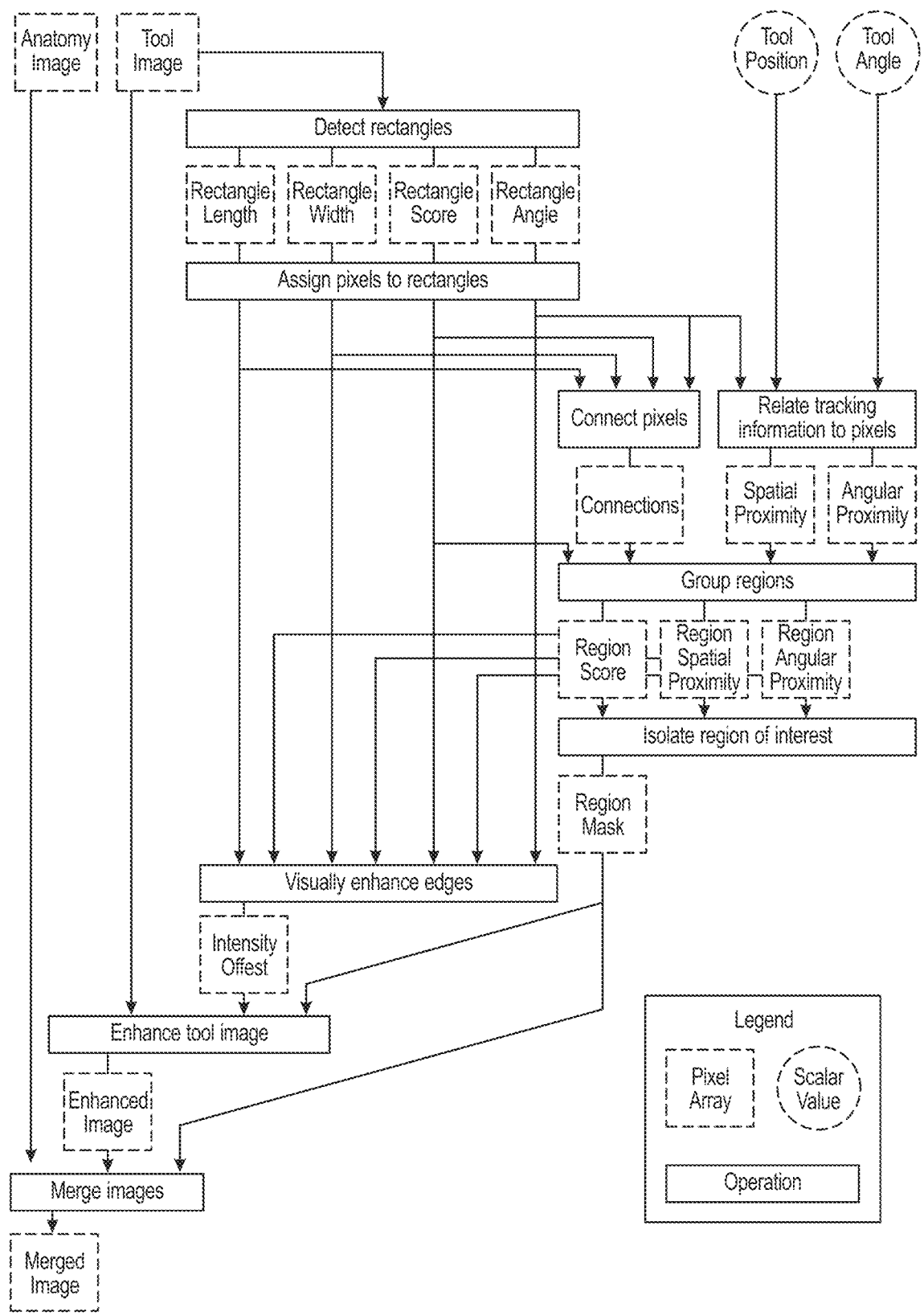
FIG. 21 is a flow chart for detecting the presence and location of a radio-dense effecter in an image of a surgical site.

The steps of one method implemented by the imaging software are shown in the chart of FIG. 21. Several parameters are available to optimize the method for particular classes of surgical tools. All steps have been designed to be straightforward to implement on a graphics processing unit, such as the GPU of the image processing device 122 (FIG. 1), which performs optimally when the same computational operation can be performed at all pixels in an image simultaneously. In the present implementation, the entire operation can be applied to a standard size image in half a second with a consumer-grade graphics card, which suffices for most usage patterns.

Figure 22:
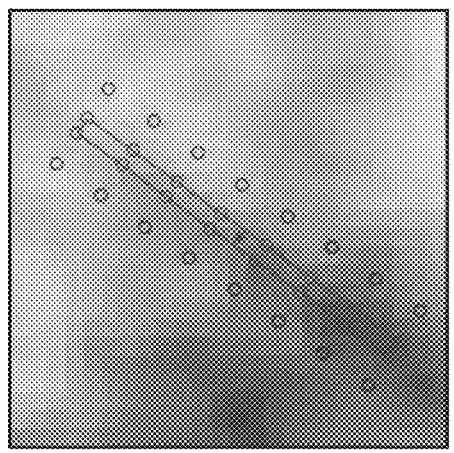
FIG. 22 is a screen shot of an x-ray image of an effecter in a surgical site illustrating one step of the detection method in the flow chart of FIG. 21.

One step of the method is to detect rectangles within the x-ray image. Each pixel is assigned a score that represents how well a dark rectangular pattern can be fitted to the neighborhood centered on the pixel. A rectangle is defined by its angle, width, and length. The score for a particular rectangle is the sum of the differences in the intensity values between points along the inside of the long edges of the rectangle and points along the outside (FIG. 22). This score calculation is performed for many different possible rectangles over a range of angles, widths, and lengths, and the highest score is reported, along with the corresponding angle, width, and length.

When tracking a radio-dense tool that is especially thick, the difference calculation can also be performed at multiple depths in the interior of the rectangle. This ensures that the rectangle has a homogeneous interior. The intensity difference formula can be clamped to a narrow range of possible values, and scaled by a fractional exponent, so that especially large intensity differences will not have a disproportionate influence on the final score.

Figure 23:
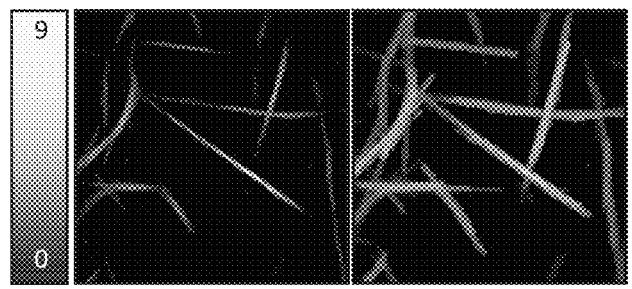
FIG. 23 is a screen shot of an x-ray image of an effecter in a surgical site illustrating a further step of the detection method in the flow chart of FIG. 21.

In a next step, pixels of the x-ray image are assigned to the rectangles. This step extends the results from rectangle detection. For each pixel, the neighborhood around the pixel is searched for the highest-scoring rectangle that overlaps it (FIG. 23). This score is reported, along with the corresponding angle, width, and length. This step is needed because rectangles have corners and intersections, and the pixels at these locations are not centered on the rectangle that best contains them.

Figure 24:
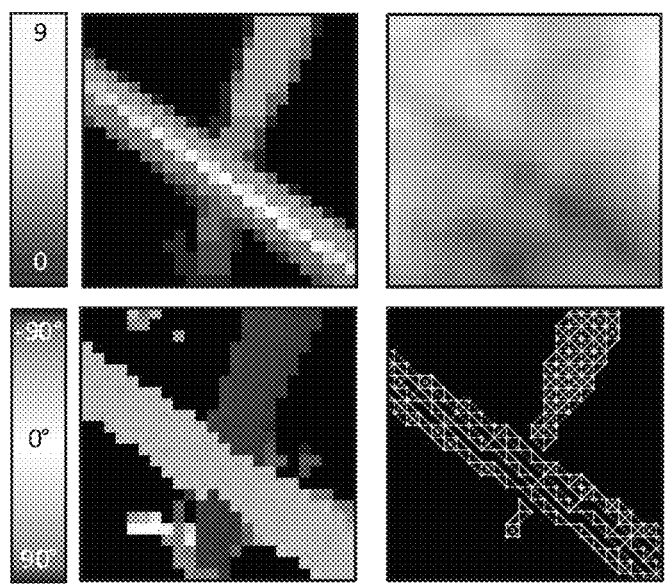
FIG. 24 is a screen shot of an x-ray image of an effecter in a surgical site illustrating another step of the detection method in the flow chart of FIG. 21.

In an X-ray image, a surgical tool may comprise multiple connected rectangles, so it is preferable to join the multiple rectangles together into a single contiguous region. In order to determine whether or not pixels belong to the same region, for two adjacent pixels, each of which has been assigned a rectangle score, angle, width, and length from the previous steps, the connection criterion is the sum of the differences in the rectangle scores, angles, widths, and lengths (FIG. 24). If the connection criterion falls below a threshold, the pixels share a connection. The relative contributions of the scores, angle, widths, and lengths can be weighted in order to control their influence on the criterion. Each pixel has 8 neighbors to which it might potentially be connected. This operation is performed at each pixel for all 8 directions. To reduce computation time, connections between pixels with very low rectangle scores can be ignored.

Figure 25:
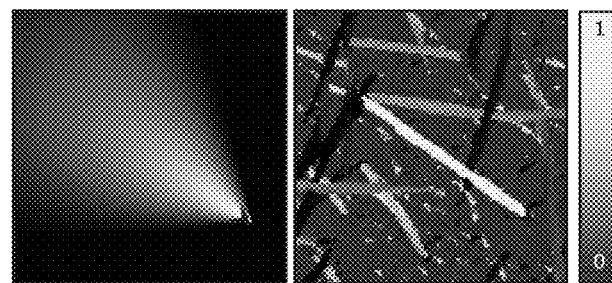
FIG. 25 is a screen shot of an x-ray image of an effecter in a surgical site illustrating a subsequent step of the detection method in the flow chart of FIG. 21.

In the next step the tracking information obtained from the localizer or tracking device for the tool is related to the pixels. The tracking device provides data for the position and orientation of the tip of the surgical tool in space. This tip can be virtually projected onto the surface of the X-ray camera and related to a point and an angle within the X-ray image, as described above. For enhancement purposes, the primary interest is in rectangular image features that have a position and angle that are close to the projected tool tip. For each pixel, the distance to the projected tool tip is calculated, and the difference between the angle of the tool tip and the angle of the rectangle at the pixel is calculated. These values can be clamped and scaled with an exponent to yield weights that quantify the spatial proximity and angular proximity of the pixel to the tool tip (FIG. 25). A tool is typically a long thin object, and pixels behind the tip belong to the object while pixels in front of the tip do not. This prior knowledge can be encoded by including orientation information into the calculation of spatial proximity.

The pixels are then grouped into contiguous regions. Each region will have a unique index, a rectangle score, a spatial proximity, and an angle proximity. These values will be accessible at each pixel in the region. There are various algorithms available for this task. The algorithm used here was chosen because it can be performed at each pixel in parallel.

The region growing algorithm proceeds iteratively. At each iteration, for each of 8 possible directions, each pixel looks at its neighbor in that direction. If the pixel shares a connection with its neighbor, then they compare rectangle scores. If the neighbor has a higher score, then the pixel receives the score and the index of its neighbor. Otherwise, if the scores are equal, and the neighbor has a higher index, then the pixel receives the index of its neighbor. If the pixel shares a connection with its neighbor and the neighbor has a higher spatial proximity, then the pixel receives the spatial proximity of its neighbor. If the pixel shares a connection with its neighbor and the neighbor has a higher angular proximity, then the pixel receives the angular proximity of its neighbor. At the end of the iteration, if the index, score, spatial proximity or angular proximity have changed for any pixel in the image, then another iteration is performed. Otherwise, the algorithm halts.

When the algorithm has finished, each pixel has been assigned to a region. Each region has a unique index, and each region has the best rectangle score, spatial proximity, and angular proximity out of all the pixels in the region. These values are stored at each pixel in the region.

Figure 26:
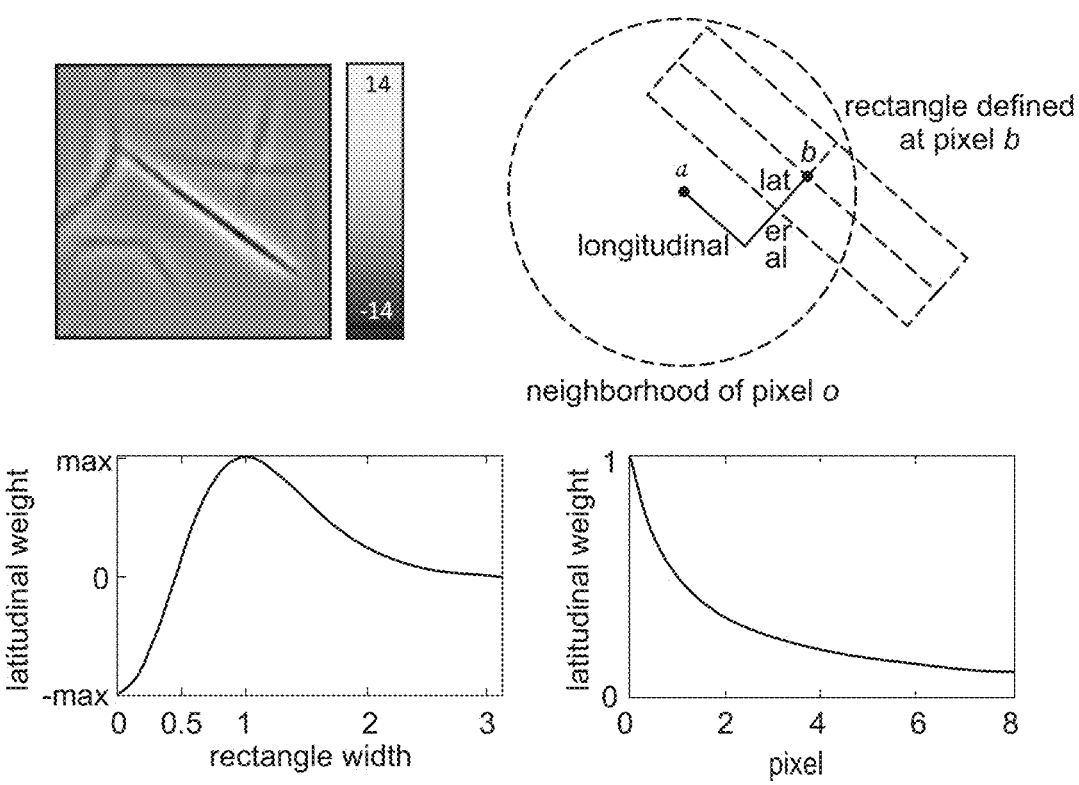
FIG. 26 is a screen shot of an x-ray image of an effecter in a surgical site illustrating yet another step of the detection method in the flow chart of FIG. 21.

Next, the regions are visually enhanced. In an X-ray image, a surgical tool should appear darker than the surrounding area. To enhance visibility, the pixels inside the region can be made darker, and the pixels outside the region lighter (FIG. 26). The changes to intensity should be smooth so that no spurious textures are introduced into the image, and so that the enhancement is robust in the presence of potential errors from the previous steps. Each pixel looks at each other pixel in the neighborhood. The score, angle, width, and length of the rectangle centered at the neighbor are found, as well as the score, spatial proximity, and angular proximity of the region to which the neighbor belongs.

The latitudinal and longitudinal axes of the neighboring rectangle are determined. The distance between the pixel and its neighbor is expressed as a sum of a latitudinal component and a longitudinal component. The latitudinal component is passed to a difference-of-Gaussians model that returns a negative value for pixels within the interior of the rectangle and a positive value in the exterior. The longitudinal component is passed to a hyperbolic model that returns a fraction that approaches 0 as the longitudinal distance grows. The offset to the pixel contributed by this neighbor is a product of the rectangle score, region score, spatial proximity, angular proximity, latitudinal weight, and longitudinal weight. The offsets from all neighboring pixels are added together. This step yields an intensity offset that can be used in the image merging step.

Figure 27:
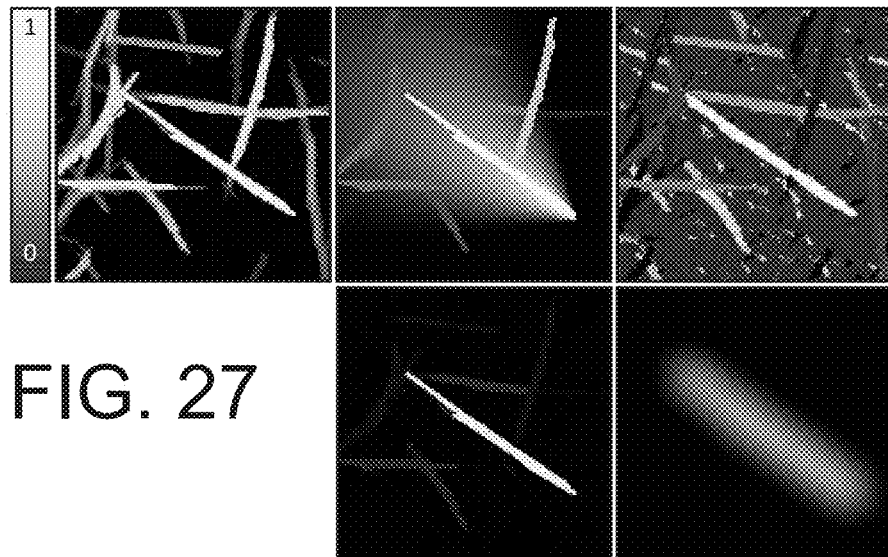
FIG. 27 is a screen shot of an x-ray image of an effecter in a surgical site illustrating one step of the detection method in the flow chart of FIG. 21.

The tracking information is then used to isolate the region of interest. The tracking information is used to weight the regions according to their proximity to the tool tip. This will generate a mask that can be used to selectively weight different parts of the image when the image is merged (FIG. 27). For each pixel, the mask value is the product of the region score, spatial proximity, and angle proximity. This value can be thresholded and scaled with an exponent to suppress irrelevant regions of the image. The edges of the regions are often jagged and do not exactly correspond to the tool. It is thus necessary to expand the region and smooth the boundaries so that the final merged image will not have any visually unpleasant discontinuities. We accomplish this with morphological dilation, followed by convolution with a Gaussian kernel. The values of the pixels in the mask are clamped to between 0 and 1. A value of 0 indicates that the pixel does not belong to the region of interest; a value of 1 indicates that the pixel fully belongs to the region of interest.

In the next step, the entire tool image is enhanced. The intensity offset image is added to the original image of the tool. The resulting sum may now have pixels outside the acceptable intensity range of 0 to 255. To bring the intensities back to an acceptable range, and to further improve the contrast around the edges of the radio-dense material, the histogram of the intensities within the mask region of the image sum is constructed in order to determine low and high quantiles. All intensities in the sum are scaled linearly so that the low quantile is now 0 and the high quantile is now 255. This yields an enhanced tool image.

Figure 28:
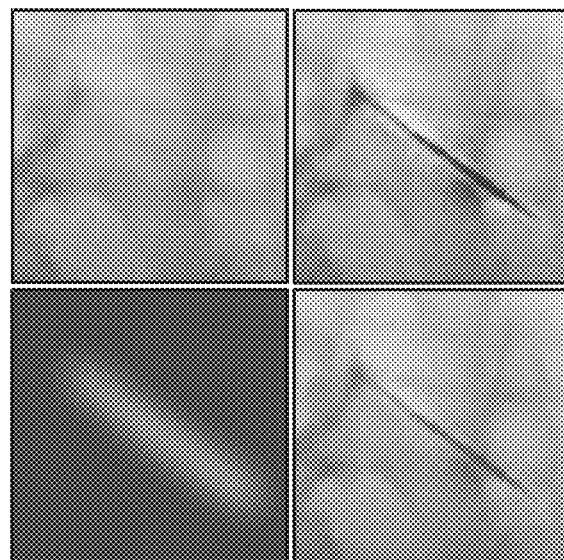
FIG. 28 is a screen shot of an x-ray image of a surgical site in which the effecter has been detected and the metal mask of the effecter enhanced within the image.

Finally, the enhanced tool image is added to the anatomical image. At pixels where the mask value is high, the enhanced tool image predominates, while at pixels where the mask value is low, the anatomical image predominates. The maximum and minimum ratios of the two images are chosen so that neither image is ever completely suppressed. This final merged image is displayed to the user as depicted in the screen shot of FIG. 28.

The present disclosure should be considered as illustrative and not restrictive in character. It is understood that only certain embodiments have been presented and that all changes, modifications and further applications that come within the spirit of the disclosure are desired to be protected.

What is claimed is:

1. A method for generating a display of an image of a patient's internal anatomy and of a radio-dense effecter in a surgical field during a medical procedure, the method comprising:
    acquiring a first image of the surgical field with an imaging device, the first image at least including the patient's internal anatomy;
    acquiring a second image of the surgical field with the imaging device, the second image at least including the radio-dense effecter;
    tracking movements of the radio-dense effecter within the surgical field with a tracking device;
    determining an overlaid image with an image processor by overlaying the second image on the first image such that the radio-dense effecter in the second image is positioned relative to the patient's internal anatomy in the first image in a same manner as the radio-dense effecter is actually positioned relative to the patient's internal anatomy in the surgical field, the overlaid image being updated over time in accordance with the tracked movements of the radio-dense effecter by moving the second image with respect to the first image; and
    displaying the overlaid image on a display screen.

2. The method of claim 1, the acquiring the second image further comprising:
    determining, with the image processor, the second image based on the first image.

3. The method of claim 1, wherein:
    the imaging device is an x-ray imaging device configured to acquire images of the surgical field with an adjustable x-ray dosage;
    the first image is acquired by the x-ray imaging device with a first x-ray dosage; and
    the second image is acquired by the x-ray imaging device with a second x-ray dosage that is less than the first x-ray dosage.

4. The method of claim 1 further comprising:
    acquiring a third image of the surgical field with the imaging device, the third image at least including the radio-dense effecter at a different position within the surgical field compared to the second image; and
    updating the overlaid image with the image processor by overlaying the third image on the first image such that the radio-dense effecter in the third image is positioned relative to the patient's internal anatomy in the first image in a same manner as the radio-dense effecter is actually positioned relative to the patient's internal anatomy in the surgical field.

5. The method of claim 1, the acquiring the second image further comprising:
    altering the second image with the image processor.

6. The method of claim 5, the altering the second image further comprising:
    filtering the second image with the image processor.

7. The method of claim 5, the altering the second image further comprising:
    reducing, with the image processor, an intensity of a portion of the second image corresponding to the patient's internal anatomy relative to a portion of the second image corresponding to the radio-dense effecter.

8. The method of claim 5, the altering the second image further comprising:
    replacing, with the image processor, a portion of the second image corresponding to the radio-dense effecter with a mask of the radio-dense effecter.

9. The method of claim 5, the altering the second image further comprising:
    altering, with the image processor, the second image to include a slug at a position within the second image corresponding to a position of a working tip of the radio-dense effecter within the surgical field.

10. The method of claim 9, wherein a configuration of the slug changes if the imaging device used to acquire the first image is moved.

11. The method of claim 9, wherein:
    the slug includes a central element and a second element representing a point on the radio-dense effecter offset from the working tip along a longitudinal axis of the radio-dense effecter; and
    an orientation of the second element relative to the central element depends on the angular orientation of the radio-dense effecter relative to the surgical field.

12. The method of claim 11, wherein the central element is a dot or a circle and the second element is a concentric circle that is larger than the dot or the circle.

13. The method of claim 11, wherein the central element is a dot or a circle and the second element is a non-circular element configured to represent a rotation of the radio-dense effecter about its longitudinal axis.

14. A system for displaying of an image of a patient's internal anatomy and of a radio-dense effecter in a surgical field during a medical procedure, comprising:
    an imaging device configured to acquire images of the surgical field;
    a tracking device configured to track movements of the radio-dense effecter within the surgical field;
    a display screen; and
    an image processor including a memory and a processor, the processor configured to execute program instructions stored on the memory to:
        receive a first image of the surgical field from the imaging device, the first image at least including the patient's internal anatomy;
        receive a second image of the surgical field from the imaging device, the second image at least including the radio-dense effecter;
        receive tracked movements of the radio-dense effecter within the surgical field from the tracking device;
        determine an overlaid image by overlaying the second image on the first image such that the radio-dense effecter in the second image is positioned relative to the patient's internal anatomy in the first image in a same manner as the radio-dense effecter is actually positioned relative to the patient's internal anatomy in the surgical field, the overlaid image being updated over time in accordance with the tracked movements of the radio-dense effecter by moving the second image with respect to the first image; and
    operate the display screen to display the overlaid image.

* * * * *